(12) United States Patent
Chin et al.

(10) Patent No.: US 7,867,163 B2
(45) Date of Patent: *Jan. 11, 2011

(54) INSTRUMENT AND METHOD FOR REMOTELY MANIPULATING A TISSUE STRUCTURE

(75) Inventors: Albert K. Chin, Palo Alto, CA (US); John P. Lunsford, San Carlos, CA (US); Tenny Chang, Mountain View, CA (US); Jeffrey W. Baxter, San Jose, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/333,542

(22) Filed: Dec. 12, 2008

(65) Prior Publication Data

US 2009/0131747 A1 May 21, 2009

Related U.S. Application Data

(63) Continuation of application No. 10/925,536, filed on Aug. 24, 2004, now Pat. No. 7,476,198, which is a continuation of application No. 10/773,770, filed on Feb. 6, 2004, now Pat. No. 6,976,957, which is a continuation of application No. 10/174,404, filed on Jun. 17, 2002, now abandoned, which is a continuation of application No. 09/634,132, filed on Aug. 8, 2000, now Pat. No. 6,406,425, which is a continuation of application No. 09/227,244, filed on Jan. 8, 1999, now Pat. No. 6,176,825, which is a continuation-in-part of application No. 09/102,723, filed on Jun. 22, 1998, now Pat. No. 5,895,353.

(51) Int. Cl.
*A61B 1/32* (2006.01)

(52) U.S. Cl. ............... 600/205; 600/204; 600/209; 600/157

(58) Field of Classification Search ............ 600/104, 600/205, 129, 209, 128, 127, 114, 130, 204, 600/157
See application file for complete search history.

(56) References Cited

U.S. PATENT DOCUMENTS 79,015 A 6/1868 Schulz (Continued)

FOREIGN PATENT DOCUMENTS

AU 199935034 A1 6/1999

(Continued)

OTHER PUBLICATIONS

U.S. Appl. No. 60/148,130, filed Aug. 10, 1999, Chin.

(Continued)

*Primary Examiner*—Pedro Philogene
(74) *Attorney, Agent, or Firm*—Vista IP Law Group LLP

(57) ABSTRACT

A retractor and a surgical tool are positioned within a cannula, and a dissection cradle of the retractor is positioned at the distal end of the cannula. The retractor includes a dissection cradle that is resiliently supported along an axis skewed relative to the axis of the cannula. The dissection cradle, in operation, is extended to cradle the target vessel, and the retractor may be fully extended to urge the vessel away from the axis of the cannula to isolate a side branch for exposure to a surgical tool. The retractor includes a hollow support and a spray nozzle disposed in the distal end of the retractor to form an irrigation system and lens washer that can be selectively positioned to direct the spray of irrigation fluid at a remote surgical site or at an endoscopic lens.

26 Claims, 13 Drawing Sheets

U.S. PATENT DOCUMENTS

| | | |
|---|---|---|
| 1,083,386 A | 1/1914 | Chapman |
| 1,422,826 A | 7/1922 | Brown |
| 1,683,708 A | 9/1928 | Wappler |
| 1,727,495 A | 9/1929 | Wappler |
| 1,731,069 A | 10/1929 | Herman |
| 1,741,461 A | 12/1929 | Herman |
| 1,798,902 A | 3/1931 | Raney |
| 1,867,624 A | 7/1932 | Hoffman |
| 1,881,250 A | 10/1932 | Tomlinson |
| 1,978,495 A | 10/1934 | Landau |
| 2,001,169 A | 5/1935 | Wallace |
| 2,002,594 A | 5/1935 | Wappler |
| 2,004,559 A | 6/1935 | Wappler et al. |
| 2,011,169 A | 8/1935 | Wappler |
| 2,012,937 A | 9/1935 | Beuoy |
| 2,028,635 A | 1/1936 | Wappler |
| 2,162,681 A | 6/1939 | Ryan |
| 2,220,720 A | 11/1940 | Jett |
| 2,227,727 A | 1/1941 | Leggiadro |
| 2,281,190 A | 4/1942 | Bertalan et. al. |
| 2,316,297 A | 4/1943 | Southerland |
| 2,840,070 A | 6/1958 | Tofflemire |
| 2,821,190 A | 1/1959 | Chase |
| 2,868,206 A | 1/1959 | Stoesser |
| 2,944,552 A | 7/1960 | Canon |
| 3,185,155 A | 5/1965 | Slaten |
| 3,224,320 A | 12/1965 | Knudsen |
| 3,297,022 A | 1/1967 | Wallace |
| 3,313,294 A | 4/1967 | Uddenberg |
| 3,336,916 A | 8/1967 | Edlich |
| 3,357,433 A | 12/1967 | Fourestier et al. |
| 3,568,677 A | 3/1971 | Nolan et al. |
| 3,613,682 A | 10/1971 | Naylor |
| 3,625,202 A | 12/1971 | Oyoshirhara |
| 3,805,793 A | 4/1974 | Wright |
| 3,835,841 A | 9/1974 | Terada |
| 3,856,016 A | 12/1974 | Davis |
| 3,857,386 A | 12/1974 | Ashbell |
| 3,866,601 A | 2/1975 | Russell |
| 3,882,854 A | 5/1975 | Hulka |
| 3,924,608 A | 12/1975 | Mitsui |
| 3,934,115 A | 1/1976 | Peterson |
| 3,980,861 A | 9/1976 | Fakunaga |
| RE29,088 E | 12/1976 | Shaw |
| 4,011,872 A | 3/1977 | Komiya |
| 4,031,898 A | 6/1977 | Hiltebrandt et al. |
| 4,038,987 A | 8/1977 | Komiya |
| 4,052,980 A | 10/1977 | Grams et al. |
| 4,132,227 A | 1/1979 | Ibe |
| 4,175,545 A | 11/1979 | Termanini |
| 4,178,920 A | 12/1979 | Cawood et al. |
| 4,190,042 A | 2/1980 | Sinnreich |
| 4,196,734 A | 4/1980 | Harris |
| 4,232,660 A | 11/1980 | Coles |
| 4,257,420 A | 3/1981 | Terayama |
| 4,359,052 A | 11/1982 | Staub |
| 4,362,160 A | 12/1982 | Hiltebrandt |
| 4,369,768 A | 1/1983 | Vukovic |
| 4,372,295 A | 2/1983 | Heckele |
| 4,418,692 A | 12/1983 | Guay |
| 4,423,727 A | 1/1984 | Widran et al. |
| 4,428,746 A | 1/1984 | Mendez |
| 4,440,170 A | 4/1984 | Golden et al. |
| 4,493,321 A | 1/1985 | Leather |
| 4,493,711 A | 1/1985 | Chin et al. |
| 4,499,898 A | 2/1985 | Knepshield |
| 4,499,899 A | 2/1985 | Lyons, III |
| 4,516,574 A | 5/1985 | Hewes, Jr. |
| 4,516,575 A | 5/1985 | Gerhard et al. |
| 4,556,058 A | 12/1985 | Green |
| 4,557,255 A | 12/1985 | Goodman |
| 4,562,832 A | 1/1986 | Wilder et al. |
| 4,586,919 A | 5/1986 | Taheri |
| 4,587,968 A | 5/1986 | Price |
| 4,597,030 A | 6/1986 | Brody et al. |
| 4,597,389 A | 7/1986 | Ibrahim et al. |
| 4,600,940 A | 7/1986 | Sluyter |
| 4,607,622 A | 8/1986 | Fritch |
| 4,638,802 A | 1/1987 | Okada |
| 4,646,738 A | 3/1987 | Trott |
| 4,649,917 A | 3/1987 | Karasawa |
| 4,651,733 A | 3/1987 | Mobin-Uddin |
| 4,653,476 A | 3/1987 | Bonnet |
| 4,654,024 A | 3/1987 | Crittenden |
| 4,656,999 A | 4/1987 | Storz |
| 4,657,018 A | 4/1987 | Hakky |
| 4,662,068 A | 5/1987 | Polonsky |
| 4,667,655 A | 5/1987 | Ogiu et al. |
| 4,700,694 A | 10/1987 | Shishido |
| 4,702,246 A | 10/1987 | Ellis et al. |
| 4,726,370 A | 2/1988 | Karasawa et al. |
| 4,744,363 A | 5/1988 | Hasson |
| 4,745,908 A | 5/1988 | Wardle |
| 4,754,754 A | 7/1988 | Garito et al. |
| 4,759,348 A | 7/1988 | Cawood |
| 4,759,364 A | 7/1988 | Boebel |
| 4,762,120 A | 8/1988 | Hussein |
| 4,768,508 A | 9/1988 | Chin et al. |
| 4,772,093 A | 9/1988 | Abele et al. |
| 4,773,394 A | 9/1988 | Reichstein et al. |
| 4,779,611 A | 10/1988 | Grooters et al. |
| 4,793,346 A | 12/1988 | Mindich |
| 4,819,620 A | 4/1989 | Okutsu |
| 4,819,633 A | 4/1989 | Bauer et al. |
| 4,821,718 A | 4/1989 | Uldall |
| 4,838,246 A | 6/1989 | Hahn et al. |
| 4,858,595 A | 8/1989 | Buess et al. |
| 4,862,874 A | 9/1989 | Kellner |
| 4,865,019 A | 9/1989 | Phillips |
| 4,867,138 A | 9/1989 | Kubota et al. |
| 4,869,268 A | 9/1989 | Yoon |
| 4,874,375 A | 10/1989 | Ellison |
| 4,877,016 A | 10/1989 | Kantor et al. |
| 4,909,789 A | 3/1990 | Taguchi et al. |
| 4,919,129 A | 4/1990 | Weber, Jr. et al. |
| 4,924,851 A | 5/1990 | Ognier et al. |
| 4,924,882 A | 5/1990 | Donovan |
| 4,932,952 A | 6/1990 | Wojciechowicz, Jr. |
| 4,936,842 A | 6/1990 | D'Amelio et al. |
| 4,950,278 A * | 8/1990 | Sachse et al. ............... 606/170 |
| 4,959,067 A | 9/1990 | Muller |
| 4,966,596 A | 10/1990 | Kuntz et al. |
| 4,985,030 A | 1/1991 | Melzer et al. |
| 4,991,565 A | 2/1991 | Takahashi et al. |
| 4,994,062 A | 2/1991 | Nishigaki et al. |
| 4,997,419 A | 3/1991 | Lakatos et al. |
| 4,997,436 A | 3/1991 | Oberlander |
| 4,998,527 A | 3/1991 | Meyer |
| 4,998,972 A | 3/1991 | Chin et al. |
| 5,007,907 A | 4/1991 | Nishigaki et al. |
| 5,007,908 A | 4/1991 | Rydell |
| 5,011,490 A | 4/1991 | Fischell et al. |
| 5,013,312 A | 5/1991 | Parins et al. |
| 5,020,514 A | 6/1991 | Heckele |
| 5,025,778 A | 6/1991 | Silverstein et al. |
| 5,026,370 A | 6/1991 | Lottick |
| 5,026,383 A | 6/1991 | Nobles |
| 5,035,232 A | 7/1991 | Lutze et al. |
| 5,037,433 A | 8/1991 | Wilk et al. |
| 5,047,038 A | 9/1991 | Peters et al. |
| 5,049,154 A | 9/1991 | Quadri |
| 5,053,041 A | 10/1991 | Ansari et al. |
| 5,100,420 A | 3/1992 | Green et al. |
| 5,171,311 A | 12/1992 | Rydell et al. |

| | | | | | |
|---|---|---|---|---|---|
| 5,181,919 A | 1/1993 | Bergman et al. | 5,489,290 A | 2/1996 | Furnish |
| 5,188,630 A | 2/1993 | Christoudias | 5,490,836 A | 2/1996 | Desai |
| 5,190,541 A | 3/1993 | Abele et al. | 5,496,317 A | 3/1996 | Goble et al. |
| 5,195,505 A | 3/1993 | Josefsen | 5,496,345 A | 3/1996 | Kieturakis et al. |
| 5,197,971 A | 3/1993 | Bonutti | 5,501,654 A | 3/1996 | Failla et al. |
| 5,201,752 A | 4/1993 | Brown et al. | 5,505,686 A | 4/1996 | Willis et al. |
| 5,213,093 A | 5/1993 | Swindle | 5,507,755 A | 4/1996 | Gresl et al. |
| 5,217,001 A | 6/1993 | Nakao et al. | 5,509,922 A | 4/1996 | Aranyi et al. |
| 5,217,441 A | 6/1993 | Shichman | 5,511,564 A | 4/1996 | Wilk |
| 5,230,621 A | 7/1993 | Jacoby | 5,512,037 A | 4/1996 | Russell et al. |
| 5,251,613 A | 10/1993 | Adair | 5,514,151 A | 5/1996 | Fogarty et al. |
| 5,258,006 A | 11/1993 | Rydell et al. | 5,514,153 A | 5/1996 | Bonutti |
| 5,259,366 A | 11/1993 | Reydel et al. | 5,518,502 A | 5/1996 | Kaplan et al. |
| 5,269,753 A | 12/1993 | Wilk | 5,522,830 A | 6/1996 | Aranyi |
| 5,269,785 A | 12/1993 | Bonutti | 5,533,496 A | 7/1996 | De Faria-Correa et al. |
| 5,271,380 A | 12/1993 | Riek et al. | 5,535,759 A | 7/1996 | Wilk |
| 5,271,385 A | 12/1993 | Bailey | 5,536,251 A | 7/1996 | Evard et al. |
| 5,273,026 A | 12/1993 | Wilk | 5,549,605 A | 8/1996 | Hahnen |
| 5,275,608 A | 1/1994 | Forman et al. | 5,549,636 A | 8/1996 | Li |
| 5,279,546 A | 1/1994 | Mische et al. | 5,549,637 A | 8/1996 | Crainich |
| 5,284,128 A | 2/1994 | Hart | 5,551,947 A | 9/1996 | Kaali |
| 5,284,478 A | 2/1994 | Nobles et al. | 5,553,496 A | 9/1996 | Nishiyama et al. |
| 5,290,284 A | 3/1994 | Adair | 5,554,101 A | 9/1996 | Matula et al. |
| 5,291,010 A * | 3/1994 | Tsuji ................... 250/208.1 | 5,558,620 A | 9/1996 | Heckele et al. |
| 5,300,036 A | 4/1994 | Mueller et al. | 5,564,615 A | 10/1996 | Bishop et al. |
| 5,312,423 A | 5/1994 | Rosenbluth et al. | 5,569,164 A | 10/1996 | Lurz |
| 5,318,564 A | 6/1994 | Eggers | 5,569,183 A | 10/1996 | Kieturakis |
| 5,318,586 A | 6/1994 | Ereren | 5,569,244 A | 10/1996 | Hahnen |
| 5,320,115 A | 6/1994 | Kenna | 5,569,274 A | 10/1996 | Rapacki et al. |
| 5,322,503 A | 6/1994 | Desai | 5,569,291 A | 10/1996 | Privitera et al. |
| 5,334,150 A | 8/1994 | Kaali | 5,571,100 A | 11/1996 | Goble et al. |
| 5,336,231 A | 8/1994 | Adair | 5,575,756 A | 11/1996 | Karasawa et al. |
| 5,337,736 A | 8/1994 | Reddy | 5,588,581 A | 12/1996 | Conlon et al. |
| 5,339,803 A | 8/1994 | Mayzels et al. | 5,591,183 A | 1/1997 | Chin |
| 5,345,927 A | 9/1994 | Bonutti | 5,599,349 A | 2/1997 | D'Amelio |
| 5,346,504 A | 9/1994 | Ortiz et al. | 5,601,580 A | 2/1997 | Goldberg et al. |
| 5,352,219 A | 10/1994 | Reddy | 5,601,581 A | 2/1997 | Fogarty et al. |
| 5,354,291 A | 10/1994 | Bales et al. | 5,618,307 A | 4/1997 | Donlon et al. |
| 5,359,995 A | 11/1994 | Sewell, Jr. | 5,626,587 A | 5/1997 | Bishop et al. |
| 5,366,476 A | 11/1994 | Noda | 5,630,787 A | 5/1997 | Yabe et al. |
| 5,368,015 A | 11/1994 | Wilk | 5,630,795 A | 5/1997 | Kuramoto et al. |
| 5,370,109 A | 12/1994 | Cuny | 5,634,584 A | 6/1997 | Okorocha et al. |
| 5,373,840 A | 12/1994 | Knighton | 5,634,924 A | 6/1997 | Turkel et al. |
| 5,374,277 A | 12/1994 | Hassler | 5,653,722 A | 8/1997 | Kieturakis |
| 5,376,076 A | 12/1994 | Kaali | 5,656,012 A | 8/1997 | Sienkiewicz |
| 5,380,291 A | 1/1995 | Kaali | 5,658,282 A | 8/1997 | Daw et al. |
| 5,383,889 A | 1/1995 | Warner et al. | 5,662,585 A | 9/1997 | Willis et al. |
| 5,385,572 A | 1/1995 | Nobles et al. | 5,662,588 A | 9/1997 | Iida |
| 5,386,818 A | 2/1995 | Schneebaum et al. | 5,662,662 A | 9/1997 | Bishop et al. |
| 5,391,178 A | 2/1995 | Yapor | 5,665,096 A | 9/1997 | Yoon |
| 5,395,367 A | 3/1995 | Wilk | 5,667,480 A | 9/1997 | Knight et al. |
| 5,395,383 A | 3/1995 | Adams et al. | 5,669,906 A | 9/1997 | Grossi et al. |
| 5,397,335 A | 3/1995 | Gresl et al. | 5,673,840 A | 10/1997 | Schulze et al. |
| 5,403,312 A | 4/1995 | Yates et al. | 5,680,982 A | 10/1997 | Schulze et al. |
| 5,411,466 A | 5/1995 | Hess | 5,683,349 A | 11/1997 | Makower et al. |
| 5,411,483 A | 5/1995 | Loomas et al. | 5,685,820 A | 11/1997 | Riek et al. |
| 5,417,697 A | 5/1995 | Wilk et al. | 5,688,269 A | 11/1997 | Newton et al. |
| 5,419,309 A | 5/1995 | Biehl | 5,690,606 A | 11/1997 | Slotman |
| 5,423,813 A | 6/1995 | Kaiser et al. | 5,695,448 A | 12/1997 | Kimura et al. |
| 5,424,877 A | 6/1995 | Tsuyuki et al. | 5,700,236 A | 12/1997 | Sauer et al. |
| 5,425,355 A | 6/1995 | Kulick | 5,702,408 A | 12/1997 | Wales et al. |
| 5,425,357 A | 6/1995 | Moll et al. | 5,702,412 A | 12/1997 | Popov et al. |
| 5,431,151 A | 7/1995 | Riek et al. | 5,704,372 A | 1/1998 | Moll |
| 5,441,041 A | 8/1995 | Sauer et al. | 5,704,534 A | 1/1998 | Huitema et al. |
| 5,441,498 A | 8/1995 | Perkins | 5,707,389 A | 1/1998 | Louw et al. |
| 5,447,513 A | 9/1995 | Davison et al. | 5,713,505 A | 2/1998 | Huitema |
| 5,448,990 A | 9/1995 | De Faria-Correa | 5,716,352 A | 2/1998 | Viola et al. |
| 5,450,842 A | 9/1995 | Tovey et al. | 5,716,505 A | 2/1998 | Scherer |
| 5,452,732 A | 9/1995 | Bircoll | 5,718,714 A | 2/1998 | Livneh |
| 5,460,629 A | 10/1995 | Shlain et al. | 5,720,761 A | 2/1998 | Kaali |
| 5,468,248 A | 11/1995 | Chin et al. | 5,722,934 A | 3/1998 | Knight et al. |
| 5,474,057 A | 12/1995 | Makower et al. | 5,725,479 A | 3/1998 | Knight et al. |
| 5,486,155 A | 1/1996 | Muller et al. | 5,728,119 A | 3/1998 | Smith |

| | | | | | | |
|---|---|---|---|---|---|---|
| 5,730,748 A | 3/1998 | Fogarty et al. | | 6,899,670 B2 | 5/2005 | Peng |
| 5,738,628 A | 4/1998 | Sierocuk et al. | | 6,963,792 B1 | 11/2005 | Green |
| 5,743,880 A | 4/1998 | Hlavka | | 6,972,028 B2 | 12/2005 | Chin |
| 5,749,870 A | 5/1998 | Gloth et al. | | 6,976,957 B1 | 12/2005 | Chin et al. |
| 5,752,966 A | 5/1998 | Chang | | 7,033,357 B2 | 4/2006 | Baxter et al. |
| 5,759,150 A | 6/1998 | Konou et al. | | 7,066,875 B2 | 6/2006 | Knighton et al. |
| 5,759,183 A | 6/1998 | VanDusseldorp | | 7,097,665 B2 | 8/2006 | Stack |
| 5,759,188 A | 6/1998 | Yoon | | 7,146,984 B2 | 12/2006 | Stack |
| 5,762,606 A | 6/1998 | Minnich | | 7,211,040 B2 | 5/2007 | Knighton e |
| 5,766,169 A | 6/1998 | Fritzsch et al. | | 7,214,180 B2 | 5/2007 | Chin |
| 5,766,215 A | 6/1998 | Muri et al. | | 7,226,409 B2 | 6/2007 | Steven Peng |
| 5,772,576 A | 6/1998 | Knighton et al. | | 7,264,587 B2 | 9/2007 | Chin |
| 5,779,728 A | 7/1998 | Lunsford | | 7,288,096 B2 | 10/2007 | Chin |
| 5,795,331 A | 8/1998 | Cragg et al. | | 7,326,178 B1 | 2/2008 | Lunsford et al. |
| 5,817,013 A | 10/1998 | Ginn et al. | | 7,344,536 B1 | 3/2008 | Lunsford |
| 5,827,175 A * | 10/1998 | Tanaka ................. 600/104 | | 7,364,657 B2 | 4/2008 | Mandrusov |
| 5,843,121 A | 12/1998 | Yoon | | 7,384,423 B1 | 6/2008 | Chin |
| RE36,043 E | 1/1999 | Knighton | | 7,398,781 B1 | 7/2008 | Chin |
| 5,857,961 A | 1/1999 | Vanden Hoek et al. | | 7,431,725 B2 | 10/2008 | Stack |
| 5,871,496 A | 2/1999 | Ginn et al. | | 7,476,198 B1 | 1/2009 | Chin et al. |
| 5,881,720 A | 3/1999 | Vinogtadov et al. | | 7,479,104 B2 | 1/2009 | Lau |
| 5,895,352 A | 4/1999 | Kleiner | | 7,485,092 B1 | 2/2009 | Stewart |
| 5,895,353 A | 4/1999 | Lunsford | | 2002/0183593 A1 | 12/2002 | Chin et al. |
| 5,897,487 A | 4/1999 | Ouchi | | 2003/0187460 A1 | 10/2003 | Chin |
| 5,908,429 A | 6/1999 | Yoon | | 2003/0187461 A1 | 10/2003 | Chin |
| 5,913,870 A | 6/1999 | DeFonzo et al. | | 2003/0236544 A1 | 12/2003 | Lunsford |
| 5,916,213 A | 6/1999 | Haissaguerre et al. | | 2004/0097792 A1 | 5/2004 | Moll |
| 5,921,993 A | 7/1999 | Yoon | | 2004/0102804 A1 | 5/2004 | Chin |
| 5,925,058 A | 7/1999 | Smith | | 2004/0153098 A1 | 8/2004 | Chin |
| 5,928,135 A | 7/1999 | Knight et al. | | 2004/0153101 A1 | 8/2004 | Bolduc |
| 5,928,138 A | 7/1999 | Knight et al. | | 2004/0181242 A1 | 9/2004 | Stack |
| 5,938,620 A | 8/1999 | Daxer | | 2004/0216748 A1 | 11/2004 | Chin |
| 5,957,923 A | 9/1999 | Hahnen et al. | | 2004/0236231 A1 | 11/2004 | Knighton |
| 5,957,936 A | 9/1999 | Yoon et al. | | 2004/0236310 A1 | 11/2004 | Chin |
| 5,984,937 A | 11/1999 | Morse et al. | | 2005/0192613 A1 | 9/2005 | Lindsay |
| 5,984,938 A | 11/1999 | Yoon | | 2005/0247320 A1 | 11/2005 | Stack |
| 5,984,939 A | 11/1999 | Yoon | | 2005/0261712 A1 | 11/2005 | Balbierz |
| 5,993,384 A | 11/1999 | Lunsford et al. | | 2005/0266109 A1 | 12/2005 | Chin |
| 6,036,713 A | 3/2000 | Kieturakis | | 2005/0267499 A1 | 12/2005 | Stack |
| 6,059,802 A | 5/2000 | Ginn | | 2006/0052660 A1 | 3/2006 | Chin |
| 6,071,232 A | 6/2000 | Knighton | | 2006/0079915 A1 | 4/2006 | Chin |
| 6,080,102 A | 6/2000 | Konou et al. | | 2006/0116746 A1 | 6/2006 | Chin |
| 6,120,434 A | 9/2000 | Kimura et al. | | 2006/0206121 A1 | 9/2006 | Chin |
| 6,123,689 A | 9/2000 | To | | 2006/0270900 A1 | 11/2006 | Chin |
| 6,129,661 A | 10/2000 | Iafrati et al. | | 2006/0271032 A1 | 11/2006 | Chin |
| 6,162,173 A | 12/2000 | Chin et al. | | 2006/0287574 A1 | 12/2006 | Chin |
| 6,176,825 B1 | 1/2001 | Chin et al. | | 2006/0287734 A1 | 12/2006 | Stack |
| 6,186,825 B1 | 2/2001 | Rogiel et al. | | 2007/0060932 A1 | 3/2007 | Stack |
| 6,234,958 B1 | 5/2001 | Snoke et al. | | 2007/0118206 A1 | 5/2007 | Colgan |
| 6,277,137 B1 | 8/2001 | Chin | | 2007/0162067 A1 | 7/2007 | Lunsford |
| 6,296,608 B1 * | 10/2001 | Daniels et al. .............. 600/104 | | 2007/0198043 A1 | 8/2007 | Cox |
| 6,312,442 B1 | 11/2001 | Kieturakis et al. | | 2007/0219571 A1 | 9/2007 | Balbierz |
| 6,348,037 B1 | 2/2002 | Chin et al. | | 2007/0238917 A1 | 10/2007 | Peng |
| 6,361,543 B1 | 3/2002 | Chin et al. | | 2007/0276432 A1 | 11/2007 | Stack |
| 6,387,043 B1 | 5/2002 | Yoon | | 2008/0039879 A1 | 2/2008 | Chin |
| 6,406,425 B1 | 6/2002 | Chin et al. | | 2008/0065122 A1 | 3/2008 | Stack |
| 6,520,975 B2 | 2/2003 | Branco | | 2008/0097523 A1 | 4/2008 | Bolduc |
| 6,558,313 B1 | 5/2003 | Knighton et al. | | 2008/0103365 A1 | 5/2008 | Lunsford et al. |
| 6,562,051 B1 | 5/2003 | Bolduc | | 2008/0132892 A1 | 6/2008 | Lunsford |
| 6,648,898 B1 | 11/2003 | Baxter | | 2008/0145345 A1 | 6/2008 | Mandrusov |
| 6,660,016 B2 | 12/2003 | Lindsay | | 2008/0145469 A1 | 6/2008 | Chin |
| 6,673,087 B1 | 1/2004 | Chang | | 2008/0306333 A1 | 12/2008 | Chin |
| 6,702,813 B1 | 3/2004 | Baxter et al. | | 2008/0306335 A1 | 12/2008 | Lau |
| 6,705,986 B2 | 3/2004 | Fiegel et al. | | 2009/0024156 A1 | 1/2009 | Chin |
| 6,730,020 B2 | 5/2004 | Peng et al. | | | | |
| 6,749,609 B1 | 6/2004 | Lunsford | | FOREIGN PATENT DOCUMENTS | | |
| 6,752,756 B2 | 6/2004 | Lunsford et al. | | | | |
| 6,762,368 B2 | 7/2004 | Saputro | | AU | 1999-42354 | 7/1999 |
| 6,811,546 B1 | 11/2004 | Callas | | AU | 199942354 A1 | 7/1999 |
| 6,814,696 B1 | 11/2004 | Chang et al. | | AU | 1999-035034 | 1/2000 |
| 6,814,743 B2 | 11/2004 | Chin | | AU | 719712 | 8/2000 |
| 6,830,546 B1 | 12/2004 | Chin et al. | | AU | 2007-203086 | 7/2007 |
| 6,884,248 B2 | 4/2005 | Bolduc | | CA | 2 244 164 | 1/1997 |

| | | |
|---|---|---|
| CA | 2 274 270 | 12/1999 |
| CA | 2 279 661 | 2/2000 |
| CA | 2 592 766 | 6/2007 |
| DE | 24 15 263 A1 | 10/1975 |
| DE | 3525917 A1 | 2/1986 |
| DE | 3942589 A1 | 7/1991 |
| EP | 0 131 347 | 1/1985 |
| EP | 0 243 714 A2 | 11/1987 |
| EP | 0 341 943 | 11/1989 |
| EP | 0681811 A2 | 3/1995 |
| EP | 0 664 104 | 7/1995 |
| EP | 0 681 811 A2 | 11/1995 |
| EP | 0 409 569 | 1/1997 |
| EP | 0 761 171 | 3/1997 |
| EP | 0 761 171 A2 | 3/1997 |
| EP | 0 761 171 B1 | 3/1997 |
| EP | 0761171 | 3/1997 |
| EP | 00769270 | 4/1997 |
| EP | 0 867 148 | 9/1998 |
| EP | 0 980 673 A2 | 2/2000 |
| EP | 0 980 673 | 12/2000 |
| FR | 2 265 344 | 10/1975 |
| GB | 2 082 459 | 3/1982 |
| GB | 2 195 540 | 4/1988 |
| JP | 7-27043 | 1/1995 |
| JP | 2802244 | 7/1998 |
| JP | 11-172954 | 6/1999 |
| JP | 11-225282 | 8/1999 |
| JP | 2000-037389 | 2/2000 |
| JP | 2007-509702 | 4/2007 |
| JP | 2007-175478 | 7/2007 |
| SU | 112367 | 6/1958 |
| SU | 510235 | 4/1976 |
| SU | 1371689 A1 | 2/1988 |
| WO | WO 91/08710 | 6/1991 |
| WO | WO 92/20291 | 11/1992 |
| WO | WO 94/18881 | 9/1994 |
| WO | 95/10982 | 4/1995 |
| WO | WO 95/10982 | 4/1995 |
| WO | WO 95/19737 | 7/1995 |
| WO | WO 96/01130 | 1/1996 |
| WO | WO 96/30072 | 10/1996 |
| WO | WO 96/36287 | 11/1996 |
| WO | WO 97/16125 | 5/1997 |
| WO | 97/268831 | 7/1997 |
| WO | WO 97/26831 | 7/1997 |
| WO | WO 97/33522 | 9/1997 |
| WO | WO 97/37701 | 10/1997 |
| WO | WO 98/02084 | 1/1998 |
| WO | WO 98/02102 | 1/1998 |
| WO | WO 98/06451 | 2/1998 |
| WO | WO 00/40139 | 7/2000 |
| WO | WO 00/40160 | 7/2000 |
| WO | WO 03/057062 A2 | 7/2003 |
| WO | WO 03/094758 A1 | 11/2003 |
| WO | WO 03/105706 | 12/2003 |
| WO | WO 2004/066828 A2 | 8/2004 |
| WO | WO 2004/066829 A2 | 8/2004 |
| WO | WO 2004/073506 | 9/2004 |
| WO | WO 2005006955 A2 | 1/2005 |
| WO | WO 2005/044079 A2 | 5/2005 |

OTHER PUBLICATIONS

U.S. Appl. No. 60/150,737, filed Aug. 25, 1999, Chin.
U.S. Appl. No. 08/269,666, filed Jul. 1, 1994, Chin.
U.S. Appl. No. 08/502,494, filed Mar. 14, 2000, Chin et al.
U.S. Appl. No. 08/593,533, filed Jan. 24, 1996, Chin.
U.S. Appl. No. 09/133,136, filed Aug. 12, 1998, Chin.
U.S. Appl. No. 09/227,393, filed Jan. 8, 1999, Lunsford et al.
U.S. Appl. No. 09/413,012, filed Oct. 5, 1999, Chin et al.
U.S. Appl. No. 09/635,721, filed Aug. 9, 2000, Chin.
U.S. Appl. No. 09/738,608, filed Dec. 14, 2000, Chin.
U.S. Appl. No. 09/739,595, filed Dec. 15, 2000, Chiang.
U.S. Appl. No. 09/750,848, filed Dec. 27, 2000, Chin.
U.S. Appl. No. 10/345,666, filed Jan. 16, 2003, Stack.
U.S. Appl. No. 10/371,537, filed Feb. 21, 2003, Beavers.
U.S. Appl. No. 11/962,517, filed Dec. 21, 2007, Chin.
MacKenzie, The Use of Laryngoscope in Diseases of the Throat: with an essay on Hoarseness Loss of Voice, and Stridulous Breathing, in Relation to Nervo-Muscular Affection of the Larynx (1869).
Schwyzer, "On Bronchoscopy. With Report of a Case in Which a Foreign Body was Removed from the Right Lower Lobe of a Lung Through a Bronchoscope", Read before the Minnesota Academy of Medicine pp. 194-206 (Dec. 2, 1903).
Mathews, A Treatise on Diseases of the Rectum, Anus, and Signoid Flexure (1903).
Mayo, "The Surgical Treatment of Varicose Veins", The St. Paul Medical Journal, vol. VI, pp. 695-699 (1904).
Fenwick, "A Handbook of Clinical Electric-Light Cystoscopy" (1905).
Carrel et al., "Uniterrninal and Biterminal Venous Transplantations", Surgery, Gynecology and Obstetrics, vol. II, pp. 266-286 (1906).
Mayo, "Treatment of Varicose Veins", Surgery, Gynecology and Obstetrics, pp. 385-388 (1906).
Carrel et al., "Results of the Biterminal Transplantation of Veins", pp. 415-422 (1906).
Jackson, "Endothelioma of the Right Bronchus Removed by Peroral Bronchoscopy", The American Journal of the Medical Sciences, vol. CLIII, pp. 37-375 (1917).
Stern, "Resection of Obstruction at the Vesical Orifice; New Instruments Resectoscope and New Method", Journal of American Medical Association, vol. 87, No. 21, pp. 1726-1730 (1926).
Chandler, "Internal Pneumolysis: Results of 110 Consecutive Operations", The Lancet, pp. 879-882 (Oct. 19, 1935).
Hurley, "Some Practical Guiding Principles for Closed Pneumonolysis", Canad. M.A.J., vol. 56, pp. 625-627 (Jun. 1947).
Bayliss, "Closed Intrapleural Pneumonolysis", Chest, vol. XIII, pp. 479-515 (1947).
Sarot et al., "Closed Pneumonolysis (Enucleation Technique)", Chest, vol. XVI, No. 5, pp. 509-542 (Nov. 1949).
Morris et al., "Arterial Bypass Below the Knee", Surgery, Gynecology & Obstetrics, vol. 108, pp. 321-332 (Jan.-Jun. 1959).
Hall, "The Great Saphenous Vein Used in Situ as an Arterial Shunt After Extirpation of the Vein Valves", Surgery, vol. 51, No. 4, pp. 492-495 (Apr. 1962).
Linton et al., "Autogenous Saphenous Vein Bypass Grafts in Femoropopliteal Obliterative Arterial Disease", Surgery, vol. 51, No. 1, pp. 62-73 (Jan.-Jun. 1962).
Palva, "Mediastinoscopy —A New Field for Bronchologists", Acta Oto-Laryngologica, vol. 53, Issue 2 & 3 (1961), http://www.informaworld.com/smpp/content.
Lore, "Tender Grip Forceps", The American Journal of Surgery, vol. 104, pp. 84-85 (Jul. 1962).
May et al., "Arterialized in Situ Saphenous Vein", Archives of Surgery, vol. 91, No. 5, pp. 743-750 (Nov. 1965).
Steptoe, "Abdominal Laparoscopy", Laparoscopy in Gynaecology, pp. 13-25 (1967).
Favaloro, "Saphenous Vein Graft in the Surgical Treatment of Coronary Artery Disease", The Journal of Thoracic and Cardiovascular Surgery, vol. 58, No. 2, (Aug. 1969).
Barner et al., "Late Failure of Arterialized in Situ Saphenous Vein", Archives of Surgery, vol. 99, pp. 781-786 (Dec. 1969).
Effler et al., "The Simple Approach to Direct Coronary Artery Surgery", The Journal of Thoracic and Cardiovascular Surgery, vol. 62, No. 4, pp. 503-510 (Oct. 1971).
Nagovitsyn, "Varicocide Treatment of Varicose Veins of the Lower Extremities" (1971).
Koontz et al., "Factors Influencing Patency of the Autogenous Vein-Femoropoliteal Bypass Grafts: An Analysis of 74 Cases", Surgery, vol. 71, No. 5, pp. 753-759 (May 1972).
Rizk et al., "Vascular Endoscopy", Radiology, vol. 106, No. 1, pp. 33-35 (Jan. 1973).
Balasegaram, "Hepatic Surgery: A Review of a Personal Series of 95 Major Resections", The Australian and New Journal of Surgery, vol. 42, No. 1, pp. 1-10 (Aug. 1972).

Brody et al., "Changes in Vein Grafts Following Aorto-Coronary Bypass Induced by Pressure and Ischemia", The Journal of Thoracic and Cardiovascular Surgery, vol. 64. No. 6, pp. 847-854 (Dec. 1972).

Jones et al., "Lesions Observed in Arterial Autogenous Vein Grafts", Cardiovascular Surgery, pp. 198-210 (1972).

Kern et al., "The Intimal Proliferation in Aortic-Coronary Saphenous Vein Grafts: Light and electron microscopic studies", American Heart Journal, pp. 771-777 (Dec. 1972).

Crispin et al., "Intravascular Observation and Surgery Using the Flexible Fibrescope", The Lancet, pp. 750-751 (Apr. 7, 1973).

Abbott et al., "Structural Changes During Preparation of Autogenous Venous Grafts", Surgery, vol. 76, No. 6, pp. 1031-1040 (Dec. 1974).

Brook, "A historical review of the histology of patent autogenous vein grafts and vein patches", The Journal of Cardiovascular Surgery, vol. 16, No. 1, pp. 43-52 (Jan.-Feb. 1975).

Shepherd et al., "Physical Characteristics of Venous System in Man", Veins and their Control, pp. 171-172 (1975).

Gittes, "Operative Nephroscopy", J Urol. (Aug. 1976), http://www.ncbi.nlm.nih.gov/sites/entrez.

Cutler et al., "Autologous Saphenous vein femoropopliteal bypass: Analysis of 298 cases", Surgery, vol. 79, No. 3, pp. 325-331 (Mar. 1976).

Lukomsky et al., "Diagnosing Phasic Nature of Pulmonary Carcinoma by Means of Combined Mediastino-Laparoscopy" 1976.

Corson, "Chapter 10: Operating Room Preparation and Basic Techniques", Laparoscopy, pp. 88-102 (1977).

Gottlob, "The preservation of the venous endothelium by <<dissection without touching>> and by an atraumatic technique of vascular anastomosis", Minverva Chirurgica, vol. 32, pp. 693-700 (1977).

Tarlovskaya et al., "Endoscopic Investigations for Determining Lung Cancer Stage" (1978).

Stiles, "Technique of Saphenous vein aorta-coronary bypass grafting", The Journal of Thoracic and Cardiovascular Sugery, vol. 78, No. 2, pp. 305-308 (Aug. 1979).

May et al., "Concluding Remarks on the Therapy of Incompetent Perforating Veins", Perforating Veins, pp. 251-253 (1981).

Szilagyi et al., "Autogenous vein grafting in femoropopliteal atherosclerosis:The limits of its effectiveness", Surgery, vol. 86, No. 6, pp. 836-851 (1979).

Flemma et al., "Complications of Aortocoronary Bypass Grafting", Complications of Intrathoracic Surgery, pp. 167-177 (1979).

Ochsner et al., "The Internal Mammary Artery as a Coronary Artery Bypass Graft", Coronary Heart Surgery, pp. 120-124 (1979).

Buxton et al., "The significance of vein wall thickness and diameter in relation to the patency of femoropopliteal Saphenous vein bypass grafts", Surgery, vol. 87, No. 4, pp. 425-431 (Apr. 1980).

Hofer et al., "Morphologic Studies in Saphenous Vein Grafts for Aorto-coronary Bypass Surgery Part 1: Morphology of the Graft Using Ordinary Surgical Preparation Techniques", The Thoracic and Cardiovascular Surgeon, vol. 29, No. 1, pp. 32-37 (1981).

Bonchek, "Prevention of endothelial damage during preparation of Saphenous veins for bypass grafting", The Journal of Thoracic and Cardiovascular Surgery, vol. 79, No. 6, pp. 911-915 (Jun. 1980).

McGeachie et al., "Vein to Artery Grafts: A Quantitative Study of Revascularization by Vasa Vasorum and its Relationship to Intimal Hyperplasia" Annals of Surgery, vol. 194, No. 1, pp. 100-107 (Jul. 1981).

Gundry et al., "Intraoperative Trauma to Human Saphenous Veins: Scanning Electron Microscopic Comparison of Preparation Techniques", The Annals of Thoracic Surgery, vol. 30, No. 1, pp. 40-47 (Jul. 1980).

Buchbinder et al., "Comparison of Patency Rate and Structural Change in In Situ and Reversed Vein Arterial Bypass", Journal of Surgical Research, vol. 30. No. 3, pp. 213-222 (Mar. 1981).

Gundry et al., "Optimal preparation techniques for human Saphenous vein grafts", Surgery, vol. 88, No. 6, pp. 785-794 (Dec. 1980).

Moser, "Angioscopic Visualization of Pulmonary Emboli", Chest, vol. 77, No. 2, pp. 198-201 (Feb. 1980).

Ford et al., "Isolation of Adult Canine Venous Endothelium for Tissue Culture", In Vitro, vol. 17, No. 1, pp. 44-50 (Jan. 1980).

Delaria et al., "Leg wound complications associated with coronary revascularization", The Journal of Thoracic and Cardiovascular Surgery, vol. 81, pp. 403-407 (1981).

Fogarty et al., "Adjunctive Intraoperative Arterial Dilation: Simplified Instrumentation Technique", Archives of Surgery, vol. 116, No. 11, pp. 1391-1398 (Nov. 1981).

Logerfo et al., "An improved technique for preservation endothelial morphology in vein grafts", Surgery, vol. 90, No. 6, pp. 1015-1024 (Dec. 1981).

Greenberg et al., "Vein-Donor-Leg Cellulities After Coronary Artery Bypass Surgery", Annals of Internal Medicine, vol. 97, No. 4, pp. 565-566 (Oct. 1982).

Gunstensen et al., "Intimal Hyperplasia in Autogenous Veins Used for Arterial Replacement", The Canadian Journal of Surgery. vol. 25, No. 2, pp. 158-165 (Mar. 1982).

McGoon, "Incision Decision Advertisement", The Journal of Thoracic and Cardiovascular Surgery, vol. 83, No. 5 (May 1982).

Catinella et al., "The factors influencing early patency of coronary artery bypass vein grafts: Correlation of angiographic and ultrastructure findings", The Journal of Thoracic Cardiovascular Surgery, vol. 83, No. 5, pp. 686-700 (May 1982).

Feikes et al., "Harvesting and protection of the Saphenous vein associated with early delivery of blood cardioplegia in coronary artery bypass graft surgery", American Heart Journal, vol. 104. No. 2. Part 1, pp. 329-332 (1982).

Leather et al., "The In Situ Saphenous Vein for Arterial Bypass", Biologic and Synthetic Vascular Prostheses, pp. 351-364 (1982).

Sottiurai et al., "Autogenous Vein Grafts: Experimental Studies", Biologic and Synthetic Vascular Prostheses, pp. 311-364 (1982).

Kinney et al., "Transluminal Angioplasty: A Mechanical-Pathophysiological Correlation of its Physical Mechanisms", Radiology, vol. 153, No. 1, pp. 85-89 (Oct. 1984).

Teimourian et al., "Subcutaneous Endoscopy in Suction Lipectomy", Plastic and Reconstructive Surgery, vol. 74, No. 5, pp. 708-711 (Nov. 1984).

Gregory et al., "Composite Grafts: An Alternative to Saphenous Vein for Lower Extremity Arterial Reconstruction", The Journal of Cardiovascular Surgery, vol. 24, No. 1, pp. 53-57 (Jan.-Feb. 1983).

Hufnagel, "Chapter 1: History of Vascular Grafting", Vascular Grafting—Clinical Appliations and Techniques, pp. 1-12 (1983).

Shah et al., "In Situ Saphenous Vein Arterial Bypass", Vascular Grafting: Clinical Applications and Techniques, pp. 133-147 (1983).

Baddour et al., "Recurrent Cellulitis After Coronary Bypass Surgery", The Journal of the American Medical Journal, vol. No. 8, pp. 1049-1052 (Feb. 17, 1984).

Chin et al., "A Physical Measurement of the Mechanisms of Transluminal Angioplasty", Surgery, vol. 95, No. 2, pp. 196-201 (Feb. 1984).

Crew et al., "Carotid Surgery without Angiography", The American Journal of Surgery, vol. 148, pp. 217-220 (Aug. 1984).

Adcock et al., "Optimal Techniques for Harvesting and Preparation of Reversed Autogenous Vein Grafts for Use as Arterial Substitutes:A Review ", vol. 96, No. 5, (Nov. 1984).

Rashid et al., "Subcutaneous Technique for Saphenous Vein Harvest", The Annals of Thoracic Surgery, vol. 37, No. 2, pp. 169-170 (Feb. 1984).

Ben-Simhon et al., "Vein Harvesting by Long Blunt and Blind Dissection. A Standardized Technique in the Dog", Biomaterials, Medical Devices, and Artificial Organs, vol. 12, No. 1 & 2, pp. 51-66 (1984).

Dorsey, "Harvesting the Greater Saphenous Vein with a Subcutaneous Vein Remover", The Canadian Journal of Surgery, vol. 28, No. 1, pp. 13-14 (Jan. 1985).

Tilanus et al., "Saphenous Vein or PTFE for Femoropopliteal Bypass", Annals of Surgery, vol. 202, No. 6, pp. 780-782 (Dec. 1985).

Dorsey, "Saphenous Vein Harvesting Using a Subcutaneous Vein Remover", Minnesota Medical Association, pp. 195-198 (Mar. 1985).

Baddour, "Delayed Soft Tissue Infections in Saphenous Venectomy Limbs of Coronary Bypass Patients", Infections in Surgery, vol. 4, No. 4, pp. 243-248 (Apr. 1985).

Spears et al., "Coronary Angioscopy During Cardiac Catheterization", Journal of the American College of Cardiology, vol. 6. No. 1, pp. 93-97 (Jul. 1985).

Hulka et al., "Standard Gynecologic Techniques", Textbook of Laparoscopy, (1994).

Hobbs, "A New Approach to Short Saphenous Vein Varicosities", Surgery of Veins, pp. 301-321 (1985).

Nagovitsyn, "Operative Treatment of Acute Thromophiebitis of the Superficial Veins of the Lower Extremities" (1985).

Weaver et al., "The Lesser Saphenous Vein:Autogenous Tissue for Lower Extremity Revascularization", Journal of Vascular Surgery, vol. 5, No. 5, pp. 687-692 (May 1987).

Scher et al., "Prevention and Management of Ischemic Complications of Vein Harvest Incisions in Cardiac Surgery Case Reports", Angiology, The Journal of Vascular Diseases, vol. 37, No. 1, pp. 119-123 (Jan. 1986).

Taylor et al., "Present Status of Reversed Vein Bypass for Lower Extremity", Journal of Vascular Surgery, vol. 3, No. 2, pp. 288-297 (Feb. 1986).

Meldrum-Hanna, "Long Saphenous Vein Harvesting", The Australian and New Zealand Journal of Surgery, vol. 56, No. 12, pp. 923-924 (Dec. 1986).

Raess et al., "Lesser Saphenous Vein as an Alternative Conduit of Choice in Coronary Bypass Operations", The Annals of Thoracic Surgery, vol. 41, No. 3, pp. 334-336 (Mar. 1986).

Sanborn, "Vascular Endoscopy: Current State of the Art", British Medical Bulletin, vol. 42, No. 3, pp. 270-273 (Apr. 1986).

Grundfest et al., "The Current Status of Angioscopy and Laser Angioplasty", Journal of Vascular Surgery, vol. 5, No. 4, pp. 667-673 (Apr. 1987).

Classen et al., "The Impact of Endoscopy", Gastroenterological Endoscopy, pp. 23-26.

LeMaitre et al., "In Situ Grafting Made Easy", Archives of Surgery, vol. 123, No. 1, pp. 101-103 (Jan. 1988).

Fleisher et al., "Angioscopically Monitored Saphenous Vein Valvulotomy", Journal of Vascular Surgery, vol. 4, No. 4, pp. 360-364 (Oct. 1986).

Miller, "Endoscopic Surgery of the Upper Urinary Tract", British Medical Bulletin, vol. 43, No. 3, pp. 274-279 (1986).

Nagovitsyn, "The Endoscopic Correction of the Shin Venous Blood Flow", Vestnik Khriurgii, vol. 137, No. 11, pp. 48-51 (Nov. 1986).

Noera et al., "Microscopic Evaluation in Saphenous Veins Used as Aortocoronary Bypass Grafts", Giornale Italiano di Cardiologia, vol. 16, No. 12, pp. 1037-1042 (Dec. 1986).

Suma et al. "Vein Perfusions System" for Harvesting the Saphenous Vein Graft in Coronary Bypass Surgery, Kyobu Geka, vol. 39. No. 8, pp. 622-623 (Aug. 1986).

Mehigan, "Symposium:Vascular Application of Angioscopy and Lasers", Journal of Vascular Surgery, vol. 5, No. 4, pp. 664-666 (Apr. 1987).

Taylor et al., "Autogenous Reversed Vein Bypass for Lower Extremity Ischemia in Patients with Absent of Inadequate Greater Saphenous Vein", The American Journal of Surgery, vol. 153, pp. 505-510 (May 1987).

Hashizume et al., "Intimal Response of Saphenous Vein to Intraluminal Trauma by Simulated Angioscope Insertion", Journal of Vascular Surgery, vol. 5. No, 6, pp. 862-868 (Jun. 1987).

Spyt, "Harvesting of the Lesser Saphenous Vein", The Annals of Thoracic Surgery, vol. 43, No. 6, p. 691 (Jun. 1987).

White, "Angioscopy and Laser in cardiovascular Surgery: Current Applications and Future Prospects", Aust. N. Z. J. Surg., vol. 58, No. 271-274 (1988).

Matsumoto et al., "Direct Vision Valvulotomy in In Situ Venous Bypass", Surgery Gynecology & Obstetrics, vol. 165, No. 4 (Oct. 1987).

Classen et al., "Electronic Endoscopy—The Latest Technology", Endoscopy, vol. 19, pp. 118-123 (1987).

Delmotte, "The Electronic Video Endoscope of Tomorrow, but First, its Present Status", Acta Endoscopica, vol. 17, No. 2, pp. 89-91 (1987).

Dimitri et al., "A Quick and Atraumatic Method of Autologous Vein Harvesting Using the Subcutaneous Extraluminal Dissector". The Journal of Cardiovascular Sugery, vol. 28, No. 2, pp. 103-111 (Mar.-Apr. 1987).

Secroun, "Future Methods of Endoscopy", Acta Endoscopica, vol. 17, No. 2, pp. 92-95 (1987).

Lannerstad et al., "Effects of Different Graft Preparation Techniques on the Acute Thrombogenicity of Autologous Vein Grafts", European Surqical Research, vol. 19, pp. 395-399 (Nov.-Dec. 1987).

Towne, "Vascular Endoscopy", Perioperative Assessment in Vascular Surgery, pp. 303-313 (1987).

Chin et al., "The Effect of Valvulotomy on the Flow Rate Through the Saphenous Vein Graft: Clinical Implications", Journal of Vascular Surgery, vol. 8, No. 3, pp. 316-320 (Sep. 1988).

Wood, "Locating Previously "Stripped" Venous Systems and Harvesting of Lesser Saphenous Vein", The Annals of Thoracic Surgery, vol. 45. No. 3 (Mar. 1988).

Takemoto, "Electronic Endoscopy: Its Present and Future", Journal of Gastroenterology and Hepatology, vol. 4, pp. 75-80 (1989).

Cardella et al., "Lower-Extremity Venous Thrombosis: Comparison of Venography, Impedance Plethysmography, and Intravenous Manometry", Radiology, vol. 168, No. 1, pp. 109-112 (Jul. 1988).

Citrin et al., "Replacement of the Carotid Artery Using Nonreversed Saphenous Vein", Surgery, Gynecology & Obstetrics, vol. 167, pp. 155-157 (Aug. 1988).

Woelfle et al., "Intraoperative Assessment of In Situ Saphenous Vein Bypass Grafts by Vascular Endoscopy", European Journal Vascular Endovascular Surgery European, vol. 2, pp. 257-262 (Aug. 1988).

Patel et al., "The Use of Fiber-Optic Intraluminal Transillumination for Saphenous Vein Harvesting", Journal of Vascular Surgery, vol. 8, No. 3, pp. 346-348 (Sep. 1988).

Gaudiani et al., "An Improved Technique for the Internal Mammary Artery Coronary Bypass Graft Procedure", Journal of Cardiac Surgery, vol. 3, No. 4, pp. 467-473 (Dec. 1988).

Hauer et al., "Endoscopic Subfascial Dissection of Perforating Veins", Surgical Endoscopy, vol. 2, pp. 5-12 (1988).

Lee et al., "Hazards of Angioscopic Examination: Documentation of Damage to the Arterial Intima", American Heart Journal, vol. 116, No. 6, pp. 1530-1536 (Dec. 1988).

Rey et al., "Electronic Video Endoscopy: Preliminary Results of Imaging Modification", Endoscopy, vol. 20, pp. 8-10 (1988).

Taylor et al., "Reversed vs. In Situ: Is Either the Technique of Choice for Lower Extremity Vein Bypass?", Perspectives in Vascular Surgery, vol. 1, No. 1, pp. 35-59 (1988).

Barnes et al., "Technical Innovations in Nonreversed Translocated Saphenous Vein Bypass", Journal of Vascular Surgery, vol. 9, No. 3, pp. 499-501 (Mar. 1989).

Chin et al., "Technique Using the Fiberoptic Valvulotome for the In Situ Vein Graft", Surgery Gynecology & Obstetrics, vol. 169, No. 3, pp. 255-256 (Sep. 1989).

Hauer, "Diagnosis and surgical management of varicosities", Herz, vol. 14, No. 5, pp. 274-282 (1989).

Fogarty et al., "Combined Thrombectomy and Dilation for the Treatment of Acute Lower Extremity Arterial Thrombosis", Journal of Vascular Surgery, vol. 10, No. 5, pp. 531-534 (Nov. 1989).

Burnand, "Reversed Saphenous Vein for Femoropopliteal Bypass Grafting", Vascular Surgical Techniques An Atlas, pp. 228-234 (1989).

Chin et al., "Angioscopic Preparation for Saphenous Vein In Situ Bypass Grafting", Endovascular Surgery, pp. 74-81 (1989).

Lavee et al., "Complications of Saphenous Vein Harvesting Following Coronary Artery Bypass Surgery", The Journal of Cardiovascular Surgery, vol. 30, No. 6, pp. 989-991 (1989).

Utley et al., "Preoperative Correlates of Impaired Wound Healing After Saphenous Vein Excision", The Journal of Cardiovascular Surgery, vol. 98, No. 1, pp. 147-149 (1989).

Veith et al., Short Vein Grafts in Limb-saving Arterial Reconstructions, Journal of Vascular and Interventional Radiology, vol. 1, No. 1, pp. 57-61 (Nov. 1990).

Louagie et al., "Viability of Long-Term Cryopreserved Human Saphenous Vein", The Journal of Cardiovascular Surgery, vol. 31. No. 1. pp. 92-100 (Jan.-Feb. 1990).

Galloway, Jr. et al., "A new Device for Interactive, Image- Guided Surgery", Medical Imaging V: Image Capture, Formatting, and Display, SPIE-The International Society of Optical Engineering (Feb. 1991).

Myers et al., "Semi-closed, ex-situ, non-reversed or reversed autogenous vein grafting", The Journal of Cardiovascular Surgery, vol. 32, No. 1, pp. 110-116 (Jan. - Feb. 1991).

Bailey et al., "Laparoscopic Cholecystectomy: Experience with 375 Consecutive Patients", Ann. Surg., vol. 214, No. 4, pp. 531-540 (1991).

The Southern Surgeons Club, "A Prospective Analysis of 1518 Laparoscopic Cholecystectomies", New England Journal of Medicine, vol. 324. pp. 1073-1078 (Apr. 18,1991).

Clayman et al., "Laparoscopic Nephrectomy", The New England Journal of Medicine, vol. 324, No. 19, pp. 1370-1371 (May 9, 1991).

Lam, et al., "Surgical Procedures for Uncomplicated ("Routine") Female Stress Incontinence", The Urologic Clinics of North America, vol. 18, No. 2, pp. 327-337 (May 1991).

Couto et al., "Endoscopic ligation of perforator leg veins", The Lancet, vol. 337, p. 1480 (Jun. 15, 1991).

Milgalter et al., "A technique to harvest the inferior epigastric arteries for coronary bypass procedures", Journal of Cardiac Surgery, vol. 6, No. 2, pp. 306-310 (Jun. 1991).

Preising et al., "A Literature Review: Robots in Medicine", _Engineering in Medicine and Biology (Jun. 1991).

Owen et al., "Endoscopic ligation of perforator leg veins", Lancet, vol. 338, p. 248 (Jul. 27, 1991).

McCollum et al., "A Simple Means of Access for Harvesting the Lesser Saphenous Vein", European Journal Vascular Endovascular Surgery, vol. 5, pp. 469-470 (Aug. 1991).

Feldman, "Laparoscopic Nephrectomy", Journal of Medicine, vol. 325, No. 15, pp. 1110-1111 (Oct. 10, 1991).

Nowzaradan et al., "Laparoscopic Appendectomy for Acute Appendicitis: Indications and Current Use", Journal of Laparoendoscopic Surgery, vol. 1, No. 5, pp. 247-257 (Oct. 1991).

Spaw et al., "Laparoscopic Hemia Repair: The Anatomic Basis", Journal of Laparoendoscopic Surgery, vol. 1, No. 5, pp. 269-277 (Oct. 1991).

Stierli et al., "In Situ Femorodistal Bypass: Novel Technique for Angioscope-Assisted Intraluminal Side-Branch Occlusion and Valvulotomy. A preliminary Report", British Journal of Surgery, vol. 78, No. 11, pp. 1376-1378 (Nov. 1991).

Bailey et al., "Combined Laparoscopic Cholecystectomy and Selective Vagotomy", Surgical Laparoscopy & Endoscopy, vol. 1, No. 1, pp. 45-49 (1991).

Bergamini et al., "Experience with in situ saphenous vein bypass during 1981 to 1989: Determinant factors of long-term patency", p. 137 (1991).

Corbitt, Jr., "Laparoscopic Herniorrhaphy", Surgical Laparoscopy & Endoscopy, vol. 1, No. 1, pp. 23-25 (1991).

Cuschieri, "Variable curvature shape-memory spatula for laparoscopic surgery", Surgical Endoscopy, vol. 5, pp. 179-181 (1991).

Fitzgibbons et al., "Open Laparoscopy", Surgical Laparoscopy, pp. 87-97 (1991).

Fowler et al., "Laparoscopy-Assisted Sigmoid Resection", Surgical Laparoscopy & Endoscopy, vol. 1, No. 3, pp. 183-188 (1991).

Gazayerli, "The Gazayerli Endoscopic Retractor Model 1" Surgical Laparoscopy & Endoscopy, vol. 1, No. 2, pp. 98-100 (1991).

Zhila et al., "High Resection of the Left Testicular Vein and Ligation of the Internal Iliac Arteries by Means of Retroperitoneoscope", No. 5 (1991).

Zucker, "Laparoscopic Guided Cholecystectomy With Electrocautery Dissection", Surgical Laparoscopy, pp. 143-182 (1991).

"3rd World Congress of Endoscopic Surgery" (Jun. 18-20, 1992).

Santilli et al., "Comparison of Preoperative Standard Angiography with Preoperative Balloon Occlusion Femoral Angiography of the Lower Extremity", Journal of Investigative Surgery, vol. 6, No. 1, pp. 83-95 (Feb. 1993).

Zucker, Surgical Laparoscopy Update, pp. 59-61 (1993).

Wittens et al., "A New "Closed" In Situ Vein Bypass Technique", European Journal Vascular Endovascular Surgery, vol. 8, pp. 166-170 (1994).

Biglioli et al., "Arterial and Venous Graft Utilization in Reoperative Coronary Artery Surgery", Cardiology and Cardiac Surgery: Current Topics, pp. 399-415 (1993).

Chin et al., "Novel Technique and Instrumentation for Laparoscopic Application of Hemostatic Clips", The Journal of the American Association of Gynecologic Laparoscopists, vol. 1, No. 2, pp. 150-153 (Feb. 1994).

Chin et al., "Gasless Laparoscopy Using a Planar Lifting Technique", Journal of the American College of Surgeons, vol. 178, No. 4, pp. 401-403 (Apr. 1, 1994).

Kavoussi et al., "Telerobotic Assisted Laparoscopic Surgery: Initial Laboratory and Clinical Experience"; Urology, vol. 44, No. 1, pp. 15-19 (Jul. 1994).

Van Dijk et al., "A New "Closed" In Situ Vein Bypass Technique Results in a Reduced Wound Complication Rate", European Journal Vascular Endovascular Surgery, vol. 10, pp. 162-167 Aug. 1995).

Lumsden et al., "Subcutaneous, Video-Assisted Saphenous Vein harvest: Report of the first 30 Cases", Cardiovascular Surgery, vol. 4, No. 6, pp. 771-776 (Dec. 1996).

Tighe, Instrumentation for the Operating Room: A Photographic Manual (1994).

Dion et al., "Experimental laparoscopic aortobifemoral bypass", Surgical Endoscopy, vol. 9, pp. 894-897 (1995).

Bowersox et al., "Vascular applications of telepresence surgery: Initial feasibility studies in swine", Journal of Vascular Surgery, vol. 23, No. 2, pp. 281-287 (Feb. 1996).

Rosenthal, "Endoscopic in Situ Bypass", The Surgical Clinics of North America, vol. 75, No. 4, pp. 703-713 (Aug. 1995).

Nwasokwa et al., "Coronary Artery Bypass Graft Disease", Annals of Internal Medicine, vol. 123, No. 7, pp. 528-545 (Oct. 1995).

Davies et al., "Pathophysiology of Vein Graft Failure: A Review", European Journal Vascular Endovascular Surgery, vol. 9, pp. 7-18 (1995).

Gelijns et al., "From the Scalpel to the Scope: Endoscopic Innovations in Gastroenterology, Gynecology, and Surgery", Sources of Medical Technology: Universities and Industry, vol. V, pp. 67-96 (1995).

Lumsden et al., "Vein Harvest", Endoscopic Plastic Surgery (1995).

Sawaizumi et al., "Endoscopic Microsurgical Anastomosis: Experimental Study of microsurgical anastomosis using an endoscope", Journal of Japan Society of Plastic and Reconstructive Surgery, vol. 15, No. 12, pp. 871-879 (1995).

Tebbetts, Tebbetts Endoplastic Instrument System (1995).

Cusimano, "Minimally Invasive Cardiac Surgery for Removal of the Greater Saphenous Vein", Canadian Journal of Surgery, vol. 39 (Oct. 1996), http://www.cma.ca/index.cfm/ci.

Tevaearai et al., "Minimally Invasive Harvest of the Saphenous Vein for Coronary Artery Bypass Grafting", The Annals of Thoracic Surgery, vol. 63, pp. S119-S121 (1997).

Iafrati et al., "Endoscopic in situ bypass: A gentler dissection", Surgical Endoscopy, vol. 12, pp. 463-465 (1998).

Hannah et al., "Laparoscopic Retropubic Urethropexy", The Journal of the American Association of Gynecologic Laparoscopists, vol. 4, No. 1, pp. 47-52 (Nov. 1996).

EndoCABG System: Innovative instrumentation for endoscopic coronary artery bypass grafting (1996).

Lumsden et al., "Subcutaneous, video-assisted saphenous vein harvest", Perspectives in Vascular Surgery, vol. 7, No. 2, pp. 43-55 (1994).

Allen et al., "Endoscopic Saphenous Vein Harvesting", pp. 265-266 (1997).

McCarthy et al., "Tricuspid Valve Repair with the Cosgrove-Edwards Annuloplasty System", The Annals of Thoracic Surgery, vol. 64, pp. 267-268 (1997).

Jordan et al., "Video-assisted saphenous vein harvest: The evolution of a new technique", Journal of Vascular Surgery, vol. 26, No. 3, pp. 405-414 (Sep. 1997).

Moazami, "Minimally Invasive Greater Saphenous Vein Harvesting for Coronary Artery Bypass Surgery", Surgical Rounds, pp. 94-98 (Mar. 1997).

Johnson et al., "Endoscopic Femoral-Popliteal/Distal Bypas Grafting: A Preliminary Report", Journal of American Colleae of Surgeons. pp. 331-336 (1998).

Pierik et al., "Endoscopic versus open subfacial division of incompetent perforating veins in the treatment of venous leg ulceration: A randomized trial" Journal of Vascular Surgery, vol. 26, No. 6, pp. 1049-1054 (1997).

Davis et al., "Endoscopic Vein Harvest for Coronary Artery Bypass Grafting: Technique and Outcomes", The Journal of Thoracic and Cardiovascular Surgery, vol. 116, No. 2, pp. 228-235(Aug. 1998).

Hallock et al., "An Endoscopic Subcutaneous Dissector for Obtaining Vein Grafts", Annals of Plastic Surgery, vol. 41, No. 6, pp. 595-599 (Dec. 1998).

Morris et al., "Minimally Invasive Saphenous Vein Harvesting", The Annals of Thoracic Surgery, vol. 66, pp. 1026-1028 (1998).

Allen et al., "Endoscopic Versus Traditional Saphenous Vein Harvesting:A Prospective, Randomized Trial", pp. 26-31 (1998).

Stavridis et al., "Minimally Invasive Long Saphenous Vein Harvesting Using a Laryngoscope", The Heart Surgery Forum, vol. 1, pp. 37-40 (Jan. 30, 1998).

Tran et al., "Tunneling versus open harvest technique in obtaining venous conduits for coronary bypass surgery", European Journal of Cardo-thoracic Surgery, vol. 14, pp. 602-606 (1998).

Wilson, "Ethicon Endopath System", Minimally Invasive Vein Harvesting The Second Generation (Jun. 1998).

"Resins Aid in Bypass Surgery", Plastics Engineering, vol. LIV, No. 8 (Aug. 1998).

Dregelid et al., "Endothelial cell injury in human saphenous veins after manipulation and tweezer grasping", Journal of Cardiovascular Surgery, vol. 29, pp. 464-469 (1988).

Voellinger et al., "Video-Assisted Vein Harvest: A Single Institution's Experience of 103 Peripheral Bypass Cases", Vascular Surgery, vol. 32, No. 6, pp. 545-557 (Nov./Dec. 1998).

Akbari et al., "Saphenous Vein Bypass to Pedal Arteries in Diabetic Patients", pp. 227-232 (1998).

Belkin et al., "Nonreversed Saphenous Vein Bypass for Infrainguinal Arterial Reconstruction", Techniques in Vascular and Endovascular Surgery, pp. 233-241 (1998).

Kulbaski et al., "Video-Assisted Saphenous Vein Harvest", Techniques in Vascular and Endovascular Surgery, pp. 91-102 (1998).

Kyo et al., "Endoscopic harvest of saphenous vein graft for coronary artery bypass grafting: Saitama—Olympus technique", European Journal of Cardio-thoracic Surgery, vol. 14, Suppl. 1, pp. S94-S99 (1998).

Lacroix et al., "Classic versus Endoscopic Perforating Vein Surgery:a Retrospective Study", Acia chir bieg, vol. 98, pp. 71-75 (1998).

Stoney et al., "Lower Extremity", Comprehensive Vascular Exposures, pp. 145-182 (1998).

Brown et al., "Heparin Reduced Residual Clot Within the Lumen of Endoscopically Harvested Saphenous Veins", http://www.aats.org/annualmeeting/Abstracts/2007/T7.html (Aug. 6. 2008).

Snowden-Pencer, Inc., "Emory Endoplastic Instruments", Endoscopic Plastic Surgery, pp. 1-10 (1993).

Wengrovitz, "Wound Complications of Autogenous Subcutaneous Infrainguinal Arterial Bypass Surgery: Predisposing Factors and Management", vol. 11, No. 1, pp. 156-163 (Jan. 1990).

Iafrati, "Laparoscopic Cholecystectomy in the Community Hospital, our first 101 cases", Current Surgery, vol. 48, No. 10 (Dec. 1991).

Ashby, "Operative Choledochoscopy in Common Bile Duct Surgery", Annals of the Royal College of Surgeons of England, vol. 67, pp. 279-283 (1985).

Nezhat et al., "Salpingectomy via Laparoscopy: a new surgical approach" Journal of Laparoendoscopic Surgery (1991), http://www.ncbi.nlm.nih.gov/pubmed/1834264.

Gershman et al., "Laparoscopic Pelvic Lymphadenectomy", Journal of Laparoendoscopic Surgery, vol. 1, No. 1 (1990).

Leahy et al., "Minimally Invasive Esophagogastrectomy: An Approach to Esophagogastrectomy Through the Left Thorax", Journal of Laparoendosopic Surgery, vol. 1, No. 1, pp. 59-62 (Nov. 1990).

Flinn et al., "A comparative study of angioscopy and completion arteriography after infrainguinal bypass", Tehcnologies iin Vascular Surgery, pp. 295-305 (1992).

Dries et al., "The Influence of Harvesting Technique on Endothelial Preservation in Saphenous Veins", Journal of Surgical Research, vol. 52, No. 3, pp. 219-225 (Mar. 1992).

Taylor et al., "Technique of Reversed Vein Bypass to Distal Leg Arteries", Techniques in Arterial Surgery, pp. 109-122 (1990).

Taylor et al., "Present status of reversed vein bypass grafting: Five-year results of a modem series", Journal of Vascular Surgery, vol. 11, No. 2, pp. 193-206 (Feb. 1990).

Schmidt et al., "A Canine Model of Intimal Hyperplasia (IH) in Autogenous Vein Grafting: A Preliminary Report", Journal of Investigative Surgery, vol. 3, No. 4, pp. 357-364 (1990).

Sadick "Treatment of Varicose and Telagiectatic Leg Veins with Hypertonic Saline: A Comparative Study of Heparin and Saline", The Journal of Dermatologic Surgery and Oncology, vol. 16, No. 1, pp. 24-28 (Jan. 1990).

Sadick, "Sclerotherapy of Varicose and Telangiectatic Leg Veins: Minimal Sclerosant Concentration of Hypertonic Saline and Its Relationship to Vessel Diameter", The Journal of Dermatologic Surgery and Oncology, vol. 17, pp. 65-70 (1991).

Lamuraglia et al., "Angioscopy guided semiclosed technique for in situ bypass", Journal of Vascular Surgery, vol. 12, No. 5, pp. 601-604 (Nov. 1990).

Knighton et al., "Saphenous Vein In Situ Bypass", The American Journal of Surgery, vol. 160, pp. 294-299 (Sep. 1990).

Feinberg et al., "The use of composite grafts in femorocrural bypasses performed for limb salvage: A review of 108 consecutive case and comparison with 57 in situ saphenous vein bypasses", Journal of Vascular Surgery (1990).

Beretta et al., "Gastroepiploic artery free graft for coronary bypass", European Journal of Cardiothoracic Surgery, vol. 4, pp. 323-328 (1990).

Troidl, "Surgical Endoscopy and Sonography", Surgical Endoscopy, vol. 4, pp. 41-46 (1990).

Cotton, "Biomedical Engineering in Vascular Surgery", Annals of the Royal College of Surgeons of England, vol. 54, pp. 22-32 (1974).

Crispin, "Arterial Endoscopy", Acta Chirurgica Belgica, No. 1, pp. 59-67 (Jan. 1974).

Plecha, "An Improved Method of Harvesting Long Saphenous Vein Grafts", Archives of Surgery, vol. 108, No. 1 (Jan.-Jun. 1974).

Vollmar et al., "Vascular Endoscopy", The Surgical Clinics of North America, vol. 54, No. 1, pp. 111-122 (Feb. 1974).

Fogarty, "Combined thrombectomy and dilation for the treatment of acute lower extremity arterial thrombosis", Journal of ascular Surgery, vol. 10. No. 4, 530-534 (Oct. 1989).

Blanco, "Resins Aid in Bypass Surgery", Plastics Engineering (Aug. 1998).

O'Neill, "The Effects on Venous Endothelium of Alterations in Blood Flow Through the Vessels in Vein Walls, and the Possible Relation to Thrombosis", Annals of Surgery, vol. 126, No. 3, pp. 270-288 (Sep. 1947).

Matsumoto et al., "Direct Vision Valvulotomy for Nonreversed Vein Graft", Sugery Gynecology & Obstetrics, vol. 165, No. 2, pp. 180-182 (1987).

Hauer, "Surgery of Perforating Veins", Langenbecks Archive Chirurgie Supplement, pp. 464-465 (1992).

Pierik et al., "Subfascial Endoscopic Ligation in the Treatment of Incompetent Perforating Veins", European Journal Vascular Endovascular Surgery, vol. 9, pp. 38-41 (1995).

Gottlob, "Reconstruction of Venous Valves", Venous Valves: Morphology Function Radiology Surgery, pp. 188-213 (1986).

Berci, "Techiques for improving illumination and recording in endoscopy", Optics and Laser Technology, pp. 31-37 (Feb. 1976).

Berci, Endoscopy today and tomorrow (1976).

Shumacker, "Weglowski's Pioneering Vascular Surgery and Barriers to Progress", Current Critical Problems in Vascular Surgery, vol. 3 (1991).

Buchbinder et al., "B-mode Ultrasonic Imaging in the Preoperative Evaluation of Saphenous Vein", The American Journal, vol. 53, No. 7, pp. 368-372 (Jul. 1987).

Hoffmann, "Die subfasziale, endosopische Laser-Perforantes-Dissektion unter Berucksichtigung auch der lateralen Perforansvenen", Vasomed, vol. 9, No. 5 (1997).

Fischer, "Eine neue Generation der Varizenchirurgie", VASA, Band 20, pp. 311-318 (1991).

Jugenheimer et al., "Ergebnisse der endoskopischen Perforans-Dissektion", Der Chirurg, pp. 625-628 (Aug. 1991).

Kern et al, "Technique of coronary angioscopy" (2008), http://www.uptodate.com/patients/content/topic.do.
Frazee, "Neuroendoscopy Program" (2008), http://neurosurgery.ucla.edu/body.cfm.
Berci et al., "History of Endoscopy", Surgical Endoscopy, vol. 14, pp. 5-15 (2000).
"Ultrasound and Interventional Techniques", Surgical Endoscopy, vol. 10, No. 1 (Jan. 1996).
"Minimal Invasive Surgery", Surgical Endoscopy: Ultrasound and Interventional Techniques, vol. 10, No. 1 (Jan. 1996).
"The Eyes of the Wolf are Sharper", Surgical Endoscopy: Ultrasound and Interventional Techniques, vol. 10, No. 3 (Mar. 1996).
"Endoscopic suturing made easy", Surgical Endoscopy: Ultrasound and Interventional Techniques, vol. 9, No. 2 (Feb. 1995).
"Instruments for percutaneous nucleotomy and discoscopy", Surgical Endoscopy: Ultrasound and Interventional Techniques, vol. 3, No. 1 (1995).
"Fiberscope for vascular endoscopy", Surgical Endoscopy: Ultrasound and Interventional Techniques, vol. 3, No. 2 (1989).
"Narrow operative approach, atraumatic examination. The Karl Storz Neuro-Endoscope", Surgical Endoscopy vol. 3, No. 3 (1989).
"Fiberscope for vascular endoscopy", Surgical Endoscopy vol. 3, No. 4 (1989).
"New: Universal-Neuro-Endoscope. New application possibilities for Neurosurgery", Surgical Endoscopy vol. 4, No. 1 (1990).
Springer book advertisement, Surgical Endoscopy vol. 4, No. 4 (1990).
Richard Wolf advertisement, Surgical Endoscopy, vol. 5, No. 1 (1991).
"Why do open surgery", Surgical Endoscopy, vol. 5, No. 2 (1991).
"Minimally invasive surgery. Operating proctoscope for anal surgery", Surgical Endoscopy, vol. 5, No. 3 (1991).
"Laparoscopic Surgery . . . the Next Generation", Surgical Endoscopy, Vo. 6, No. 2 (1992).
"There's a Revolution in Surgery. USSC was there in the beginning", Surgical Endoscopy, vol. 6, No. 3 (1992).
"Cuschieri Thoracoscopic Instruments", Surgical Endoscopy, vol. 6, No. 4 (1992).
"Laparoscopic has just turned a new corner . . . ", Surgical Endoscopy, vol. 6, No. 5 (1992).
"Electronic Video Laparoscopy", Surgical Endoscopy, vol. 6, No. 6 (1992).
"Performing a Nissen just got easier, faster, and cheaper", Surgical Endoscopy, vol. 9, No. 9 (1995).
"Easy entry . . . maximizes safety . . . ", Surgical Endoscopy, vol. 9, No. 5 (1995).
"Richard-Allan Medical Has Just Bent the Rules on Endoscopic Cutting", Surgical Endoscopy, vol. 10, No. 9 (1996).
"High quality endoscopic instruments", Surgical Endoscopy, vol. 10, No. 11 (1996).
"Endoscopic Surgery of the Paranasal Sinuses and Anterior Skull Base", Endoscopy, vol. 22, No. 5 (1990).
"Karl Storz—Endoscopes for bronchoscopy", Endoscopy, vol. 23, No. 1 (1991).
"Original Karl-Storz. System Perfection", Endoscopy, vol. 23, No. 3 (1991).
"Minimally invasive surgery.Laparascopic cholecystectomy", Endoscopy, vol. 23, No. 4 (1991).
"Greater Visibility, Lighter Weight ", Endoscopy, Vo. 23, No. 5 (1991).
"A Different View on Diagnosis: (Toshiba Medical Systems) and 2 Live International Therapeutic Endoscopy Course in Mexico City Oct. 10-12, 1990". Endoscopy, vol. 22. No. 3 (1990).
ProMIS Line: The complete endoscopy program from AESCULAP, Endoscopy, vol. 28, No. 3 (1996).
"Now you can afford to change your point of view", Endoscopy, vol. 27, No. 3 (1995).
"Karl Storz endoscopes for NEODYM-YAG and C02 lasers", E 1990, Endoscopy, vol. 22, No. 1 (1990).
"Endoscopic Ultrasonography: EUS", Endoscopy, vol. 22, No. 2 (1990).
Surgical Laparoscopy & Endoscopy, vol. 1 No. 1 (1991).
Surgical Laparoscopy & Endoscopy, vol. 1, No. 2 (1991).
Surgical Laparoscopy & Endoscopy, vol. 1, No. 3 (1991).
Surgical Laparoscopy & Endoscopy, vol. 1, No. 4 (1991).
Surgical Laparoscopy & Endoscopy, vol. 2, No. 1 (1992).
Surgical Laparoscopy & Endoscopy, vol. 2, No. 2 (1992).
Surgical Laparoscopy & Endoscopy, vol. 2, No. 3 (1992).
Surgical Laparoscopy & Endoscopy, vol. 2, No. 4 (1992).
"Karl Storz Take-apart: the fully cleanable cost-effective, modular instrument solution", Surgical Laparoscopy & Endoscopy, vol. 6, No. 1 (1996).
Cuschieri, "How I Do It", Laparoscopic cholecystectomy (Mar. 1999).
"History of Endoscopy" (2008), http://wwww.alexea.org/.
"Laparoscopy" (1998), http://www.ehealthmd.com/library/laparoscopy/LAP_whatis.html.
White et al., Coronary Angioscopy, vol. 22, No. 1, pp. 20-25 (1995).
Olympus Endoscopic Accessories Price List, Effective Feb. 15, 1986.
Feldman, "Laparoscopic Nephrectomy", The New England Journal of Medicine, vol. 325, No. 15, pp. 1110-1111 (Oct. 10. 1991).
Kunlin, "Le traitement de l'ischáarteritique pas la greffe veineuse longue", Revue de Chirurgie, pp. 206-235 (Aug. 1951).
Stanley et al. Autogenous Saphenous Vein as an Arterial Graft:Clinical Status in Stanley JC (ed): Biologic and Synthetic Vascular Prostheses, New York, Gmne and Stratton, Inc. 333-349 (1982).
Cohen et al Indications for Left Ventricular Aneurysmectomy *Circulation* 1983; 67; 717-722.
Evdokimov et al., "A Combination of Electroacupuncture and Conduction Anesthesia in Operations for Varicose Dilatation of Lower Extremity Veins" , ISSN 0042-4625 (1985).
Lofgren Treatment of Long Saphenous Varicosities and Their Recurrence:A Long-Term Follow-Up, Surgery of the Veins, Grune & Stratton (1985).
Meldrum-Hanna et al. An Improved Technique for Long Saphenous Vein Harvesting for Coronary Revascularization, Annals of Thoracic Surgery 1986 42: 90-92.
Gottlob et al. Replacement of Small Veins by Autologous Grafts: Application of an Endothelium-Preserving Technique, *Vasc Endovascular Surg.* 1982: 16: 27 Vienna and New York.
Lukomskii, "Prevention of Post" (1986).
Nagovitsyn, "Endoscopic Coagulation of the Communicating Veins of the Leg in Chronic Venous Insufficiency", Sovetskaia Meditsina, vol. 12, pp. 109-110 (1987).
Buchbinder et al. B-Mode Ultrasonic Imaging in the Preoperative Evaluation of Saphenous Vein, American Surgeon, Jul. 1987, vol. 53, No. 7.
Sottiurari et al. Autogenous Vein Grafts:Experimental Studies, in Stanley JC (ed): Biologic and Synthetic Vascular Prostheses, New York, Gmne and Stratton, Inc. 311-331 (1982).
Hauer, "Operationstechnik der Endoskopischen Subjascialen Discision der Perforansvenen", Chirurg, vol. 58, pp. 172-175 (1987).
Nagovitsyn, "Endoscopic Electrocoagulation of the Communicating Crural Veins", Khirurgiia (Mosk), vol. 12, pp. 60-61 (Dec. 1987).
Secroun, "Future Methods of Endoscopy", Acta Endoscopica, vol. 17, No. 2, pp. 92-95 (1987).
Devambez et al., "Ecarteur Autostatique Pour Chirurgie de Varices", Phlebologie: Bulletin de la Societe Francaise de Phleaolociie (1988).
Nagovitsyn, "Vein-sparing operations combined with endoscopic electrocoagulation of the communicating veins", Vestnik Khirurgii, vol. 140, No. 3, pp. 92-93 (Mar. 1988).
Nagovitsyn, "Prevention of complications for endoscopic correction of the crural venous blood flow", Vestnik Khirurgii, vol. 142, No. 3, pp. 113-115 (Mar. 1989).
Bailey et al., "Laparoscopic Cholecystectomy: Experience with 375 Consecutive Patients", Ann. Surg. (Oct. 1991).
Maignien, "Splénectomie par voie cœlioscopique 1 observation", La Presse Médicate (Dec. 21-28, 1991).
Moll, "Historische Anmerkungen zur Entwicklung von Endoskopie and minimal invasiver Operations-technik", Geschichte der Medizin (1993).
Markstrom, "Intraoperativ angioskopi via infrainguinal bypass med vena saphena magna in situ", Medicinsk Rapport, vol. 89, No. 49 (1992).

Fischer, "Die chirurgishe Behandlung der Varizen Grundlagen and heutiger Stand: Surgery of Varicose Veins", Scheweiz. Rundshau Med. (PRAXIS). vol. 79, No. 7 (1990).
Devambez et al., "Self-Retaining retractor for surgery of varices", Phlebologie, vol. 41, No. 2, pp. 297-299 (1988).
*Endoscopy* [vol. 22, No. 4, 1990]: Document in German language 1990.
Vandamme, Jean-Pierre and Bonte, Jan, Vascular Anatomy in Abdominal Surgery, Thieme Medical Publishers, Inc. New York (1990).
Swobodnik, Atlas of Ultrasound Anatomy, Thieme Medical Publishers, Inc., New York (1991).
Respondent Terumo Cardiovascular Systems Corporation's Supplemental Responses to Maquet Cardiovascular L.L.C.'s Interrogatory Nos. 29, 32-33, 45-46, 51-62, 64 and 78 [redacted version with attached claim charts] Aug. 15, 2008.
Terumo's Proposed Claim Construction Oct. 31, 2008.
Maquet's Proposed Claim Constructions Oct. 31, 2008.
Maquet's Proposed Claim Constructions with Supporting Authority Nov. 19, 2008.
Public Complaint of Maquet Cardiovascular L.L.C. Under Section 337 of the Tariff Act of 1930 as Amended w/all exhibits Apr. 1, 2008.
Public Response of Respondents Terumo Corporation and Terumo Cardiovascular Systems Corporation to the Complaint and Notice of Investigation Jun. 9, 2008.
Public Amended Response of Respondents Terumo Corporation and Terumo Cardiovascular Systems Corporation to the Complaint and Notice of Investigation Oct. 27, 2008.
Respondent Terumo Cardiovascular Systems Corporation's Responses to Maquet Cardiovascular LLC's Seventh Set of Interrogatories (Nos. 91-95) Aug. 15, 2008.
Respondent Terumo Cardiovascular Systems Corporation's I Responses to Maquet Cardiovascular LLC's Third Set of Interrogatories [No. 78] Jun. 30, 2008.
Respondent Terumo Corporation's Responses to Maquet Cardiovascular LLC's Third Set of Interrogatories (No. 78) Jun. 30, 2008.
Respondent Terumo Corporation's Responses to Maquet Cardiovascular LLC's Sixth Set of Interrogatories (Nos. 82-86) Aug. 15, 2008.
Berci, "Endoscopy", 1976, ISBN 0-8385-2216-5.
"Enter a new realm", 2007, by Boston Scientific Corp.
"Vasoview competitive advantage", 2007, by Boston Scientific Corp.
"VasoView HemoPro endoscopic vessel harvesting system", 2007, by Guidant.
Initial Expert Report of Paul Mitiguy, Oct. 31, 2008.
Memorandum re VasoView Feedback, Aug. 29, 1996.
Memorandum re VasoView Continued Release Plan, Dec. 11, 1996.
VasoView 2 Thoughts by Scott C. Anderson, Oct. 10, 1996.
Excerpt from Frazier Lab Notebook No. 144, Jun. 9, 1997.
Excerpt from Frazier Lab Notebook No. 152, Jun. 9, 1997.
Orbital Dissection Cannula Product Specification, Jun. 7, 1997.
Attachment A PPAQ Approval, Design Review, Design Freeze, Apr. 15, 1997.
VasoView Oribital Dissector Dissection Cannula IFU, Mar. 14, 1997.
Senior Staff update, May 5, 1997.
Disengagement project Scope for Enhanced Orbital Dissector, Dec. 18, 1997.
Excerpt from Frazier Lab Notebook No. 144, Nov. 3, 1997.
Excerpt from Tachi Callas Lab notebook No. 152, Nov. 3, 1997.
Orbital Dissection Cannula Enhanced Version Product Specification, Nov. 4, 1997.
Attachment A PPAQ Approval, Design Review, Design Freeze, Sep. 15, 1997.
Attachment A, Nov. 4, 1997.
McCoy Lab Notebook No. 166, Sep. 5, 1997.
VasoView Ill Development Team Market Preference Data Sheet, Sep. 4, 1997.
VasoView Big Balloon & Handle Market Preference Data Sheet, Mar. 11, 1997.
Product Specification History Dissection Tools, Jun. 27, 1996.
Product Specification for VasoView Dissection Tools (Rev date Apr. 15, 1996).
Memo to file re Monthly Program Review Summaries, Jul. 9, 1996.
Memo to Total Heart Team regarding Notes from Assn of PA Annual meeting, Jan. 26, 1996.
Memo re FMEA Rationale for SVH Balloon Dissection Cannula, Jun. 24, 1996.
Memo regarding Design Review Path Freeze Criteria OMS-BDS, Jul. 1, 1996.
Product Specification VasoView Balloon Dissection System, Jun. 21, 1996.
VasoView Balloon Dissection System Design Validation Conclusions, Jul. 10, 1996.
VasoView Balloon Dissection System Market Preference Data Sheet, Jul. 2, 1996.
Email regarding Pig Lab Results, Aug. 4, 1995.
Summary of Clinical, Jul. 3, 1996.
VasoView Balloon Dissection System Market Preference Data Sheet, May 29, 1996.
Chin Letter to FDA regarding Pre-Market notification 510K for Tapered Tip Balloon Dissection Cannula, Jul. 17, 1995.
VasoView Balloon Dissection System Market Release Meeting, Jul. 11, 1996.
VVII Team Meeting, Dec. 4, 1996.
Jeffrey Wayne Baxter deposition transcript, Sep. 26, 2008.
Albert Chin deposition transcript, Sep. 10, 2008.
Edwin Hlavka deposition transcript, Sep. 8, 2008.
John Lunsford deposition transcript, Sep. 24, 2008.
Justin Williams deposition transcript, Oct. 8, 2008.
Eric Willis deposition transcript, Oct. 7, 2008.
Responses of Maquet Cardiovascular, L.L.C. to Respondents Terumo Corporation and Terumo Cardiovascular Systems Corporation's Second Set of Requests for Admission, Nov. 3, 2008.
Supplemental Responses of Maquet Cardiovascular, L.L.C. to Respondents Terumo Corporation and Terumo Cardiovascular Systems Corporation's Requests for Admission Nos. 8-56, Nov. 20, 2008.
Responses of Maquet Cardiovascular, L.L.C. to Respondents Terumo Corporation and Terumo Cardiovascular Systems Corporation's Third Set of Request for Admission, Nov. 24, 2008.
Responses of Maquet Cardiovascular L.L.C. to Certain Interrogatories from Respondents Terumo Corporation and Terumo Cardiovascular Systems Corporation's First Set of Interrogatories [Nos. 3, 5, 7, 12, 23, 45, 48, 49, 59, 62, and 69], May 23, 2008.
Responses of Maquet Cardiovascular L.L.C. to Respondents Terumo Corporation and Terumo Cardiovascular Systems Corporation's First Set of Interrogatories [Nos. 1-78], Jun. 6, 2008.
Supplemental Responses of Maquet Cardiovasular L.L.C. to Respondents Terumo Corporation and Terumo Cardiovascular Systems Corporation's Interrogatory Nos. [5, 6, 8, 14, 32, 33 & 67], Jul. 23, 2008.
Supplemental Responses of Maquet Cardiovascular L.L.C. to Respondents Terumo Corporation and Terumo Cardiovascular Systems Corporation's Interrogatory No. 21, Sep. 5, 2008.
Responses of Maquet Cardiovascular L.L.C. to Respondents Terumo Corporation and Terumo Cardiovascular Systems Corporation's Systems Corporation's Third Set of Interrogatories [Nos. 87-115], Aug. 6, 2008.
Responses of Maquet Cardiovascular L.L.C. to Respondents Terumo Corporation and Terumo Cardiovascular Systems Corporation's Fourth Set of Interrogatories [Nos. 116-148], Aug. 11, 2008.
Supplemental Responses of Maquet Cardiovascular L.L.C. to Respondents Terumo Corporation and Terumo Cardiovascular Systems Corporation's Fourth Set of Interrogatories, Sep. 12, 2008.
Second Supplemental Responses of Maquet Cardiovascular L.L.C. to Respondents Terumo Corporation and Terumo Cardiovascular Systems Corporation's Interrogatory Nos. 130, 131, 133, 134, 136 & 137, Oct. 21, 2008.
Supplemental Response of Maquet Cardiovascular L.L.C. to Respondents Terumo Corporation and Terumo Cardiovascular Systems Corporation's Interrogatory Nos. 146 & 148, Oct. 31, 2008.
Responses of Maquet Cardiovascular L.L.C. to Respondents Terumo Corporation and Terumo Cardiovascular Systems Corporation's Fifth Set of Interrogatories [Nos. 149-152], Sep. 5, 2008.
Responses of Maquet Cardiovascular L.L.C. to Respondents Terumo Corporation and Terumo Cardiovascular Systems Corporation's Sixth Set of Interrogatories [Nos. 153-155], Sep. 10, 2008.

Responses of Maquet Cardiovascular L.L.C. to Respondents Terumo Corporation and Terumo Cardiovascular Systems Corporation's Seventh Set of Interrogatories, Nov. 21, 2008.
Responses of Maquet Cardiovascular L.L.C. to Respondents Terumo Corporation and Terumo Cardiovascular Systems Corporation's Eighth Set of Interrogatories, Nov. 24, 2008.
Decision to merge reexamination and reissue proceedings for U.S. Patent No. 5,373,840 (control No. 90/004,301) mailed on Jan. 17, 1997.
"Current critical problems in vascular surgery" (1991) vol. 3, Ch 11-18, 25, 26, 29-31, 33-36, 4549, 65, ISBN 0-942219-24-4.
File History of U.S. Patent No. Re 36,043 issued on Jan. 12, 1999.
File History of U.S. Appl. No. 10/897,157 filed on Jul. 21, 2004.
File History of U.S. Appl. No. 10/052,016 filed on Jan. 16, 2002.
File History of U.S. Patent No. 7,326,178 issued on Feb. 5, 2008.
File History of U.S. Patent No. 5,993,384 issued on Nov. 19, 1999.
File History of U.S. Patent No. 5,895,353 issued on Apr. 20, 1999.
Order Granting/Denying Request for Reexamination from U.S. Appl. No. 90/004,301 Patent Application mailed on Oct. 1, 1996.
History of Endoscopy, http://laparoscopy.blogs.com/endoscopyhistory/table_of_contents/, 2005.
"The DaVinci Line", DaVinci Medical, 1992.
"Minimally Invasive Surgery: Laparoscopic Cholecystectomy", Karl Storz Endoscopy, 1992.
"Cabot Laparoscopic Irrigation System: Dissect/Lase/Cut/Irrigate/Aspirate through a single puncture", Surgical Laparoscopy & Endoscopy, 1990.
"A new sense of security in endoscopic ligation", Sugical Laparoscopy & Endoscopy, 1990.
"Preceptor", http://dictionary.reference.com/browse/preceptor 2010.
Classen et al., "The Impact of Endoscopy", Gastroenterological Endoscopy, 2002, pp. 23-26.
Samuels et al., "In Situ Saphenous Vein Arterial Bypass: A Study of the Anatomy Pertinent to its Use in Situ as a Bypass Graft with a Description of a New Venous Valvulatome", The American Surgeon, vol. 34, No. 2, pp. 122-130 (Feb. 1986).
Historical Development of VasoView by Albert Chin, Sep. 11, 2008.
Pending U.S. Appl. No. 10/897,157 filed on Jul. 21, 2004.
Handwritten Notes, Oct. 17, 1996.
Clinical Results, May 13, 1992.
Page from Tachi Callas Lab Notebook, Jul. 1, 1997.
Chin Memo regarding Saphenous Vein Harvesting, May 17, 1995.

* cited by examiner

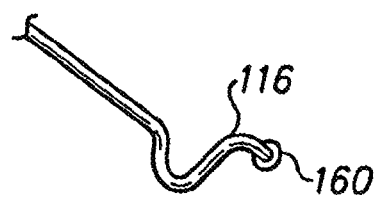
FIG. 9F
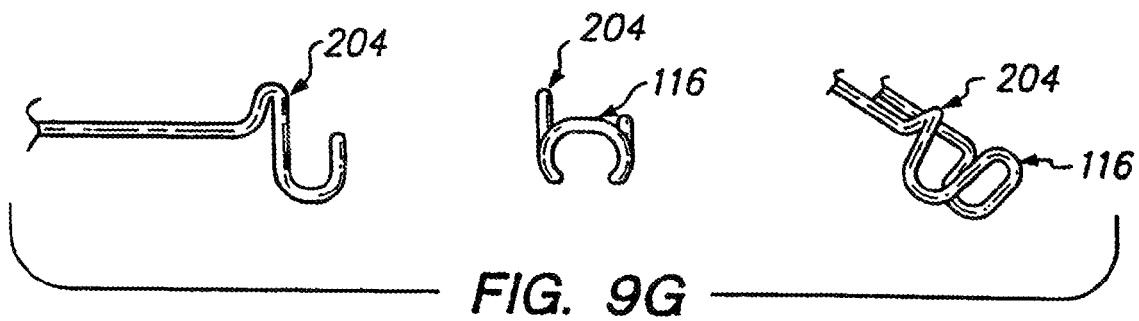
FIG. 9G
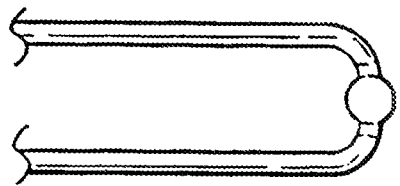 
FIG. 10A  FIG. 10B
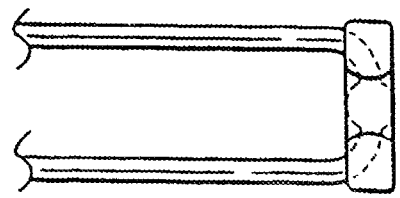 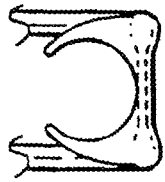
FIG. 10C  FIG. 10D

INSTRUMENT AND METHOD FOR REMOTELY MANIPULATING A TISSUE STRUCTURE

RELATED APPLICATIONS

This application is a continuation of application Ser. No. 10/925,536 filed on Aug. 24, 2004, which is a continuation of application Ser. No. 10/773,770, filed on Feb. 6, 2004, now issued as U.S. Pat. No. 6,976,957, which is a continuation of application Ser. No. 10/174,404, filed on Jun. 17, 2002, which is a continuation of application Ser. No. 09/634,132, filed on Aug. 8, 2000 which is a continuation of application Ser. No. 09/227,244 filed on Jan. 8, 1999, now issued as U.S. Pat. No. 6,176,825, which is a continuation-in-part application of application Ser. No. 09/102,723 filed on Jun. 22, 1998, now issued as U.S. Pat. No. 5,895,353.

FIELD OF THE INVENTION

This invention relates to a cannula used for endoscopic surgery, and more particularly to a cannula and method for maintaining a clear visual field for an endoscope housed within the cannula.

BACKGROUND OF THE INVENTION

Endoscopic surgery allows a surgeon to perform safe and successful procedures because of the surgeon's ability to view the surgical site through the endoscope lens. For some surgical procedures, such as dissection, the cannula housing the endoscope has a transparent blunt dissection tip through which the surgeon views the surgical site. The blunt dissection tip protects the endoscope lens from being smeared by blood or fatty tissue present at the surgical site, or from being fogged due to the moist subcutaneous environment. However, many surgical procedures cannot be performed using a blunt dissection tip. When side branches and vessel ends of a vessel must be transected to harvest the vessel, the end of the cannula must be open to allow the surgical tools to extend from the cannula. When the cannula end is open, the endoscope lens is subject to the adverse conditions described above. The surgeon is forced to repeatedly remove the cannula from the body to clean the endoscope lens. This increases the length and risks of the operation.

Some conventional schemes for cleaning an endoscope lens rely upon an endoscope with a cleaning system built within it. However, having a cleaning system within the endoscope restricts the angle of incidence at which the cleaning fluid may be propelled toward the lens to almost parallel to the lens. This results in a less effective cleansing action. Also, since the spray is being directed parallel to the lens, the surgeon cannot see the spray source and it is therefore difficult to adjust the direction of the spray. Thus, with these systems, the endoscope must still be removed on occasion for manual cleaning where the proper angle of incident spray can be obtained manually. Additionally, in procedures using gas insufflation, the gas may dry out a target vessel or other surgical site. In these situations, it is often necessary to irrigate the vessel to prevent the vessel from drying out. However, conventional endoscope washing systems are not capable of providing both endoscope lens cleaning and remote surgical site irrigation. Therefore, a remote endoscopic washing system would be desirable for more effectively cleansing the endoscope lens during a surgical procedure by allowing the surgeon to control the angle at which cleansing fluid is sprayed as well as allowing the surgeon to use the same apparatus to irrigate the surgical site itself.

SUMMARY OF THE INVENTION

In accordance with the present invention, a retractor is positioned within a cannula with a dissection cradle end of the retractor positioned at the distal end of the cannula. The retractor includes a first portion that has an axis approximately parallel to a central axis of the cannula, and a second portion that has an axis which is at an angle with respect to the central axis of the cannula. The dissection cradle is located at the distal end of the second portion of the retractor. In another embodiment, the retractor includes two legs having substantially parallel axes that selectively protrude from the distal end of the cannula. The protruding legs support the dissection cradle formed in the shape of a partial loop that is positioned in a plane skewed relative to the axes of the legs, with a bottom of the loop directed away from the cannula. Thus, in operation, when the surgeon locates a vein and side branch of interest, the surgeon extends the retractor to cradle the vein in the dissection cradle. Once cradled, the retractor may be fully extended, displacing the vein away from the axis of the cannula, causing the side branch to be isolated and exposed to a surgical tool. The surgical tool may then be extended from within the cannula to operate on the isolated and exposed side branch.

In accordance with one embodiment of the present invention, a remote irrigation system is built into the cannula. In one embodiment, one of the legs which comprise the retractor of the present invention is hollow, and is attached to a spray nozzle disposed in the distal end of the retractor. The proximal end of the hollow leg is attached to a fluid input tube which selectively provides irrigation fluid under pressure for washing the endoscope lens. When extended slightly beyond the distal end of the cannula, the spray nozzle is positioned to direct the spray of irrigation fluid at an angle approximately normal to the endoscope lens. This provides for an extremely effective cleaning action, and minimizes the need for removal of the endoscope during surgical procedures for manual cleaning. Additionally, if the surgical site itself requires irrigation, the retractor is extended out of the cannula toward the area requiring irrigation, and an irrigation fluid can be sprayed directly on the site. Finally, as the spray is directed back toward the lens, the surgeon can visually adjust the extension of the retractor to accurately direct the spray toward the lens or surgical site.

In a further embodiment, the hollow leg moves within a lumen in the cannula in fluid-resistant sliding engagement, and the fluid input tube is coupled to this lumen. In this embodiment, the maximal outer dimension of a region of the hollow leg is slightly less than a maximal inner dimension of the lumen. The slip-fit, fluid-resistant coupling of the hollow leg within the lumen allows irrigation fluid to be introduced at the proximal end of the lumen by the fluid input tube without significant leakage past the sliding juncture of the hollow leg within the lumen.

In an alternate embodiment, the hollow leg includes a semi-rigid plastic tubing, and fits within an irrigation tube which lines the inside of the lumen. The fluid input tube attaches to the irrigation tube and extends out of the cannula handle for receiving irrigation fluid. The use of flexible, semi-rigid plastic tubes provides fluid seals throughout the irrigation system to minimize leakage. In a third embodiment, the cannula contains a separate irrigation lumen which has a spray nozzle disposed in a fixed position at its distal end. The spray nozzle is positioned within the cannula to allow the proper angle of incidence for the spray to effectively clean the lens. Finally, in another embodiment, the dissection cradle is supported by only one leg, and the lumen which previously held the second leg instead is fitted with a spray nozzle directed toward the endoscope lens. An embodiment is also disclosed in which a nozzle tube situated within a cannula lumen is selectively extensible responsive to the application of hydraulic pressure.

BRIEF DESCRIPTION OF THE DRAWINGS

FIG. 7b is a side view of the retractor 112 of FIG. 7a.

FIG. 9f illustrates multiple views of a fifth alternate embodiment of cradle 116.

FIG. 9g illustrates multiple views of an embodiment of cradle 116 having a spur.

FIG. 10a illustrates a top view of an embodiment of the cradle 116 of FIG. 9c without a "C" ring.

FIG. 10b illustrates a side view of the cradle 116 of FIG. 10a.

FIG. 10c illustrates a top view of the cradle 116 of FIG. 9c with the "C" ring attached.

FIG. 10d illustrates a side view of the cradle 116 of FIG. 10c.

FIG. 11d is an alternate embodiment of the cannula-based irrigation system of FIG. 11a.

DETAILED DESCRIPTION OF THE PREFERRED EMBODIMENTS

Figure 1:
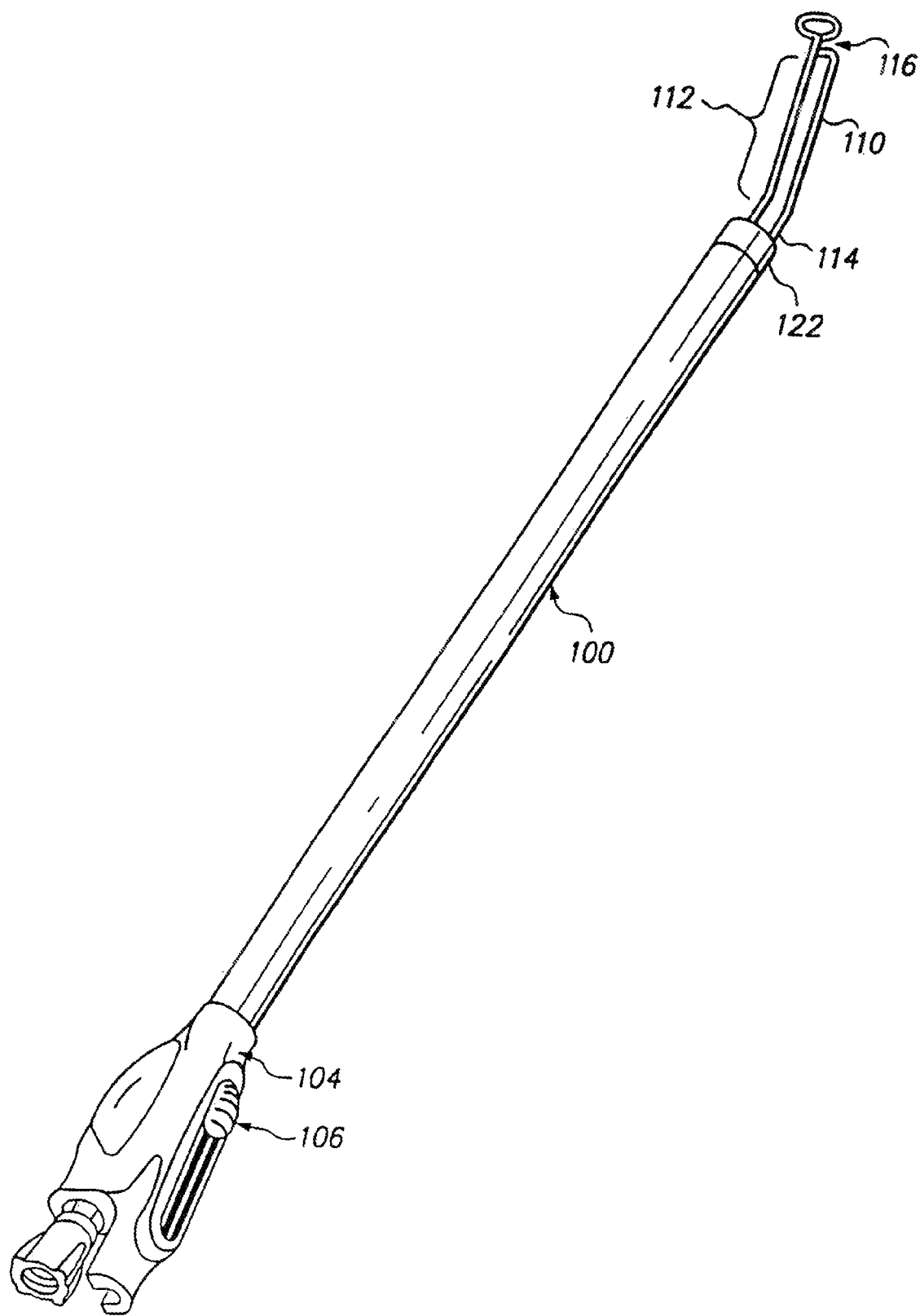
FIG. 1 is a perspective view of a preferred embodiment of cannula 100 showing retractor 112 in an extended position.

FIG. 1 illustrates a perspective view of a preferred embodiment of cannula 100 showing retractor 112 in an extended position. Cannula 100 includes an outer housing 102 of bio-inert material such as polymed UD that may be approximately 12" to 18" in length. The proximal end of the cannula 100 is disposed in handle 104 that includes a button 106 which is coupled to retractor 112 for controlling the translational movement of retractor 112, as described in more detail below.

Figure 2A:
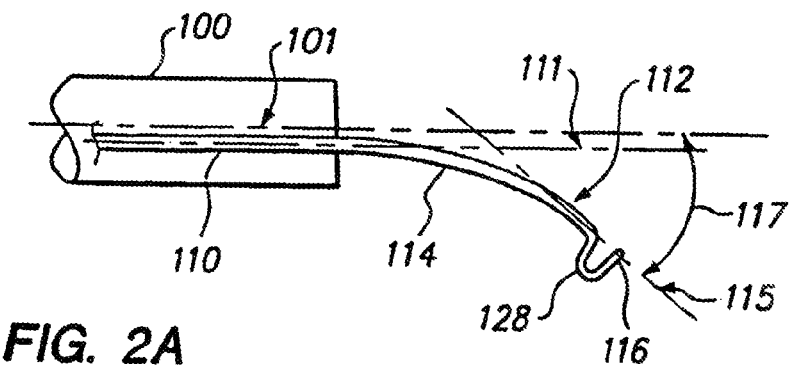
FIG. 2a is a cut-away side view of retractor 112 and cannula 100.

The distal end of the cannula houses a retractor 112, and optionally an endoscope 126 and a surgical tool 120, described below. FIG. 2a illustrates the retractor 112 in more detail. In one embodiment, retractor 112 is formed of resilient wire which has a smooth bend intermediate to a first portion 110 and a second portion 114 of the retractor. The retractor 112 is described as having two portions for ease of description, although the retractor 112 may be formed as an integrated structure. However, retractor 112 may also be manufactured from two separate portions 110, 114 that are coupled together. The first portion 110 of the retractor 112 is positioned within the cannula 100 with the axis 111 of the first portion 110 approximately parallel to the axis 101 of the cannula 100. The second portion 114 is positioned to bend away from the central axis 101 of the cannula. The angle 117 of displacement between the axis 115 of the second portion and the central axis 101 of cannula 100 may be any angle from zero to 180 degrees. The second portion 114 includes a dissection cradle 116 at the distal end of the second portion 114. The retractor 112 may be formed of bioinert material such as stainless steel, or a polymer such as nylon or polyetherimide, or other appropriately strong and resilient plastic. In one embodiment, the retractor 112 includes a coating for lubrication, insulation, and low visual glare using, for example, parylene or nylon 11.

Figure 2B:
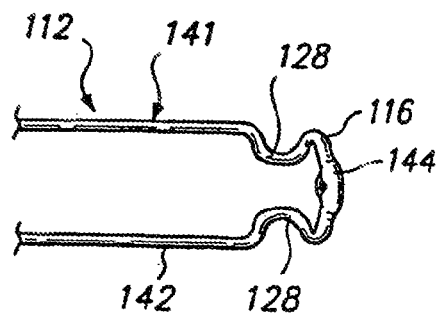
FIG. 2b is a top view of retractor 112.

FIG. 2b illustrates the retractor 112 formed with two legs. The legs 141, 142 of the retractor 112 at the distal end form the dissection cradle 116 in a loop or "U" shape, as shown in FIG. 2a. The top portion 144 of the U-shaped bend is preferably flattened to provide additional surface area for atraumatically supporting a vein 118 or vessel of interest. The side arches 128 of the dissection cradle 116 are used for skeletonizing or dissecting the vein from the surrounding tissues, as well as acting as walls to keep the vessel captured within the arch. The several embodiments of dissection cradle 116 are described in more detail below.

Figure 3A:
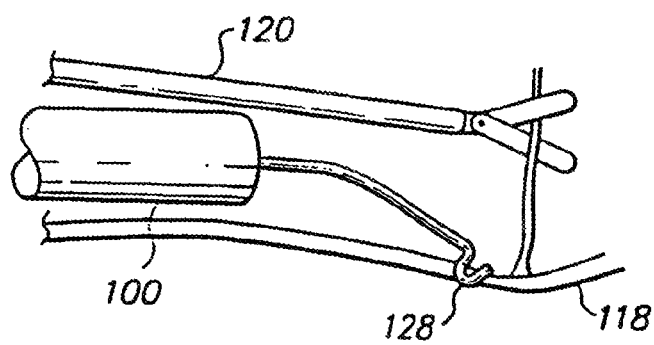
FIG. 3a is a perspective side view of cannula 100 with a saphenous vein positioned within the cradle 116.

FIG. 3a illustrates a perspective view of the cannula 100 in accordance with the present invention with the retractor fully extended, holding a saphenous vein 118, and also illustrates an external surgical tool 120 disposed adjacent the cannula 100 for performing a surgical operation, for example, severing a tributary or side branch of the vein 118. The vein is positioned within the side arches 128 of the cradle 116. The dissection cradle 116 may be used to cradle a vein, vessel, tissue or organ of interest, and surgical tool 120 may be any surgical tool suitable for performing a surgical procedure near the dissection cradle 116.

Figure 3B:
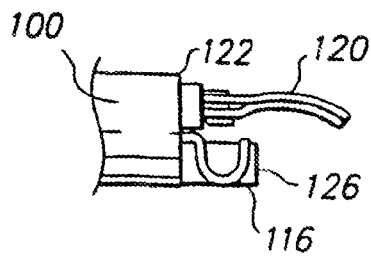
FIG. 3b is a perspective side view of the distal end 122 of cannula 100 in an embodiment in which an endoscope 126 and a surgical tool 120 are present and partially extended.
Figure 3C:
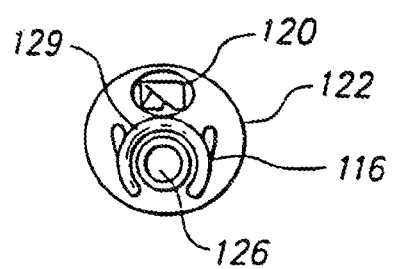
FIG. 3c is a front view of the distal end 122 of cannula 100 in which the surgical tool 120 and the retractor 116 are partially extended, and an endoscope 126 is present.

FIG. 3b illustrates a perspective view of cannula 100 in an embodiment in which the surgical tool 120 is positioned within the cannula 100, and an endoscope 126 is present. In this embodiment, cradle 116 preferably overlays the endoscope 126 with sufficient clearance to facilitate relative movements thereof. However, the endoscope may also be located adjacent the surgical tool 120. In one embodiment, endoscope 126 is positioned with cannula 100 to allow a clear field of view upon extension of the retractor 112. Surgical tool 120 is illustrated as cauterizing scissors, used to sever a tributary or side branch of a saphenous vein 118. In this embodiment, surgical tool 120 is maximally displaced from the cradle 116 at the cannula end 122. More specifically, as shown in FIG. 3c, the "U"-shaped loop 129 of the cradle 116 is closest to the surgical tool 120. This ensures that a vein 118 or other tissue of interest is retracted away from the surgical tool 120 to facilitate manipulating the surgical tool 120 relative to the side branch or other tissue.

Figure 4A:
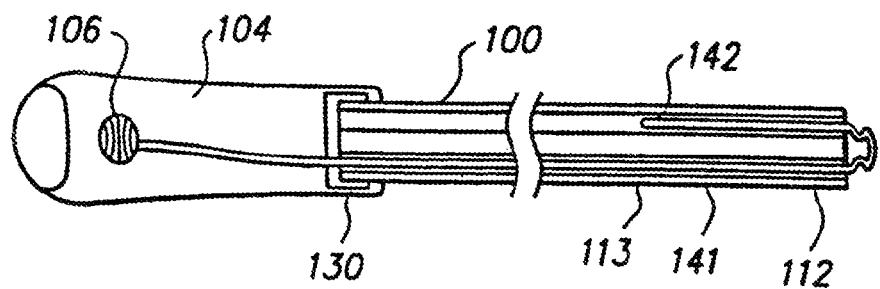
FIG. 4a is a cut-away top view of cannula 100.
Figure 4B:
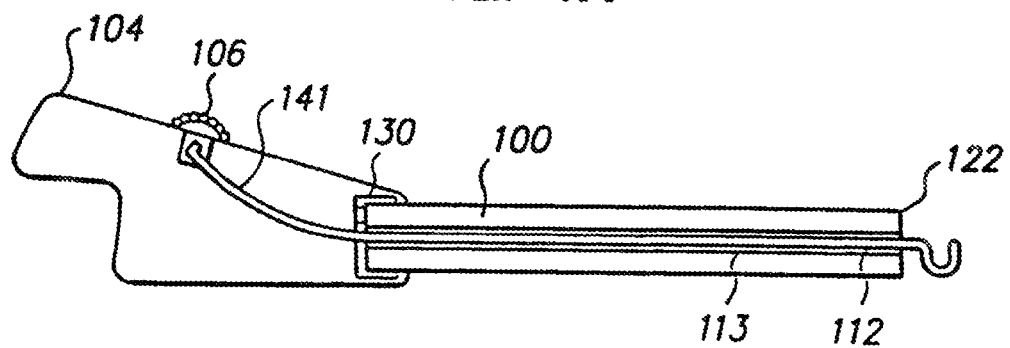
FIG. 4b is a cut-away side view of cannula 100.

FIG. 4a is a cut-away top view of cannula 100. The retractor 112 is slidably positioned within minor lumens 113 along the length of the cannula 100 within close tolerances in order to position the retractor 112 stably within the cannula 100. For example, in one embodiment retractor legs 141, 142 are approximately 0.045 inches in diameter and the lumens 113 encasing the legs 141, 142 are approximately 0.080 inches in diameter, as friction between the legs of the retractor 112 and the lumens 113 holds the retractor stably within the cannula. This configuration restricts rotational movement of the retractor to provide more stable retraction as compared with conventional retractors. The legs 141, 142 of the retractor 112 are formed of flexible, resilient material and are retained within the lumen 113 in substantially straight or flat orientation, but may return to a material bend or curve, as illustrated in FIG. 5a, as the retractor 112 is extended from the distal end of the cannula 100.

The leg 141 of the retractor 112 passes through a sliding gas or fluid seal 130 at the proximal end of the lumen 113. The leg 141 of the retractor 112 passes out of the cannula 100 and into handle 104 for attachment to a slider button 106 for facilitating translational movement of the retractor 112 from the proximal or handle end of the cannula 100. However, other types of control devices such as knobs, grips, finger pads, and the like may be linked in conventional ways to the retractor 112 in order to manually control the translational movement of retractor 112. In one configuration, the proximal end of leg 141 is bent relative to the axis of the cannula, and the button 106 is attached to the bent position of the leg 141 to facilitate moving the button 106 and the retractor 112 translationally under manual control. The button 106 preferably includes lateral grooves to prevent finger or thumb slippage during sliding manipulation of the retractor 112.

Thus, in the operation of a preferred embodiment, a user actuates the slider button 106 to extend retractor 112 out of the lumen 113 at the distal end of the cannula 100. In one embodiment, the resilient retractor 112 is formed in a smooth bend, as shown in FIG. 2a, and gradually deflects away from the central axis 101 of the cannula 100 as the retractor is extended. Upon encountering the target vessel or tissue of interest, the vessel is restrained in the cradle 116, and a lateral resilient force is exerted on the target vessel in a direction away from the cannula. The vessel is thus pushed away from the axis of the cannula 100, isolating it from surrounding tissue or adjacent vessels such as tributaries or side branches. As a tributary is thus isolated, a surgical tool 120 such as cauterizing scissors may be safely employed to operate on the tributary without harming the saphenous vein 118. When retracted into the cannula 100, the retractor 112 is again resiliently straightened or flattened.

Figure 5A:
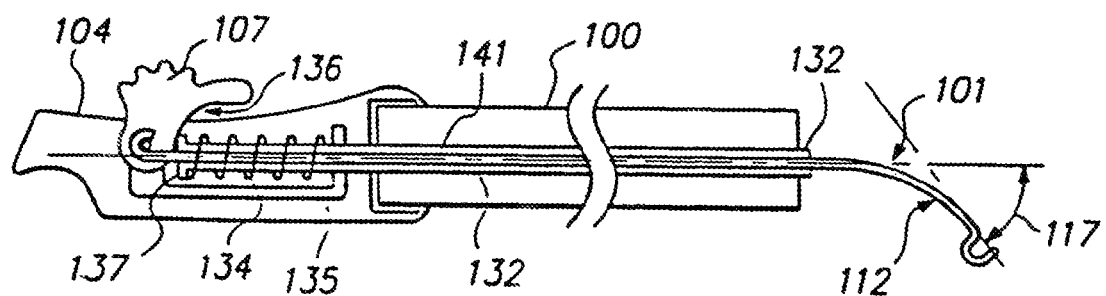
FIG. 5a is a cut-away view of a sliding tube embodiment of cannula 100 in a first position.
Figure 5B:
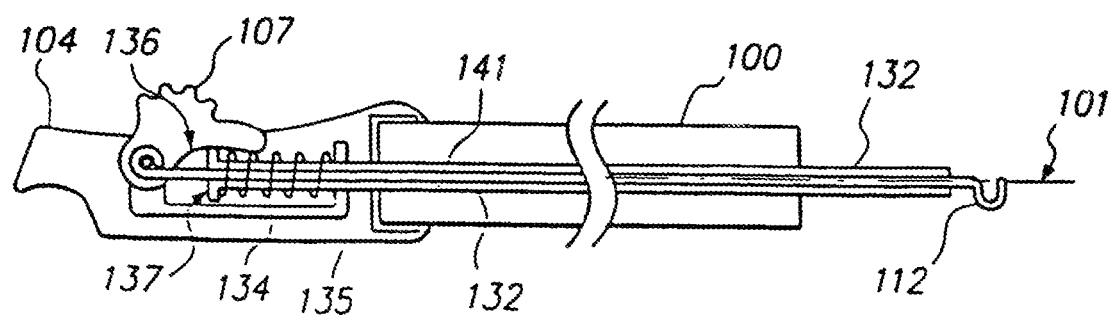
FIG. 5b is a cut-away view of the sliding tube embodiment of FIG. 5a in a second position.

In an alternate embodiment as illustrated in FIGS. 5a and 5b, a sliding tube 132 is added to provide operational versatility to cannula 100. In a first position, the sliding tube 132 is retracted and the retractor 112 protrudes from the distal end at an angle with respect to the central axis 101 of the cannula 100. In a second position, the sliding tube 132 is extended out, temporarily straightening the retractor 112. As illustrated in FIG. 5a, a sliding tube 132, in a first position encases the retractor 112 up to the point at which the retractor 112 curves away from the central axis 101 of the cannula thus allowing the retractor 112 to displace and isolate a target vessel. The proximal end of the sliding tube 132 is linked to button 107 for translationally moving retractor 112 as well as actuating the sliding tube 132. In one embodiment, as illustrated in FIG. 5a, the sliding tube 132 is in a first position with the button 107 in an upright position. A spring 134 is coupled between a support structure 135 and the proximal end 137 of the sliding tube 132. In the first position of sliding tube 132, the spring 134 is extended fully and exerts little or no force on the sliding tube 132. Of course, sliding tube 132 may be manually manipulated without linkage to a button 107.

To extend the sliding tube 100, button 107 is pushed down. As illustrated in FIG. 5b, the button 107 has a cam surface 136 which pushes on the proximal end 137 of the sliding tube 132 as the button 107 is pressed. The sliding tube 132 is pushed forward, overcoming the resilient force of spring 134, to encase the retractor 112 and decrease angle 117 between the distal end of the retractor 112 and the central axis 101 of the cannula 100. Upon releasing the button 107, the spring force urges the proximal end 137 of the sliding tube 132 back toward the first position against button 107. The sliding tube 132 is formed of material having sufficient strength to force the retractor 112 to straighten out the angle 117, and the retractor 112 is formed of resilient material having a sufficient flexibility to straighten out the angle 117 in response to a tube 132 being slid over the retractor 112, but having sufficient rigidity to cradle and dissect a target vessel. Resiliency of the retractor 112 ensures return to the downwardly-curved shape after being released from tube 132. Thus, in accordance with this embodiment, a user may employ the curved retractor for certain applications and employ the straightened form for other applications. A manual actuator may be configured in other ways than button 107 to extend the sliding tube 132 in response, for example, to being pulled up instead of pushed down.

Figure 6A:
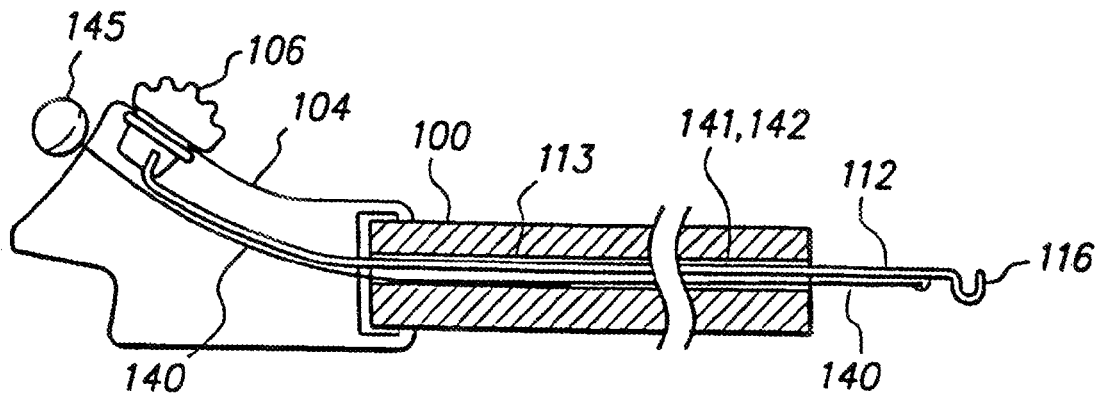
FIG. 6a is a cut-away view of an embodiment of cannula 100 having an angling device 140.
Figure 6B:
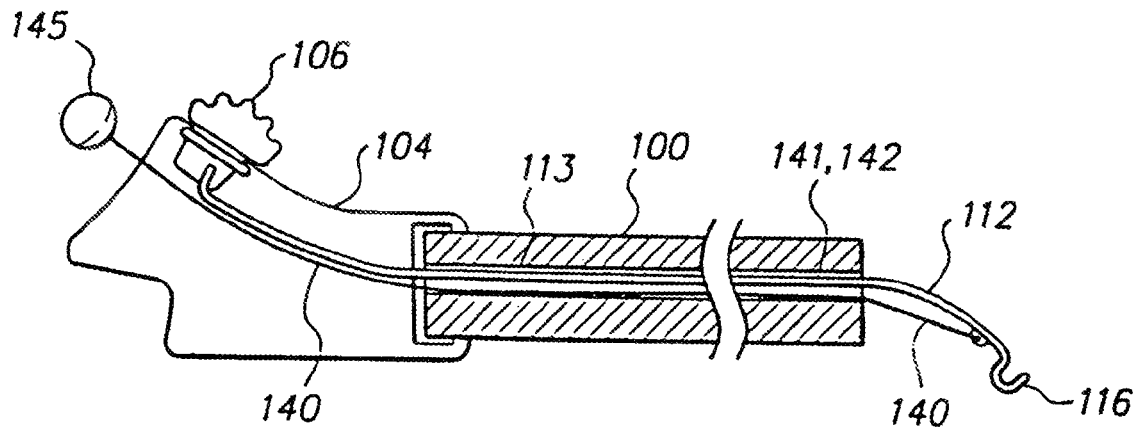
FIG. 6b is a cut-away side view of the apparatus illustrated in FIG. 6a in which the retractor 112 is extended and the angling device 140 is actuated.

Another embodiment employs a retractor 112 which has a naturally straight shape. As illustrated in FIGS. 6a and 6b, an angling device 140 is disposed between the distal end of the retractor 112 and the proximal end of the cannula. The angling device 140 may be positioned within the same lumens 113 as the retractor 112 and preferably may comprise two wires coupled to points below the cradle 116 of the retractor 112 substantially in parallel positions on each of the legs 141, 142.

Figure 6C:
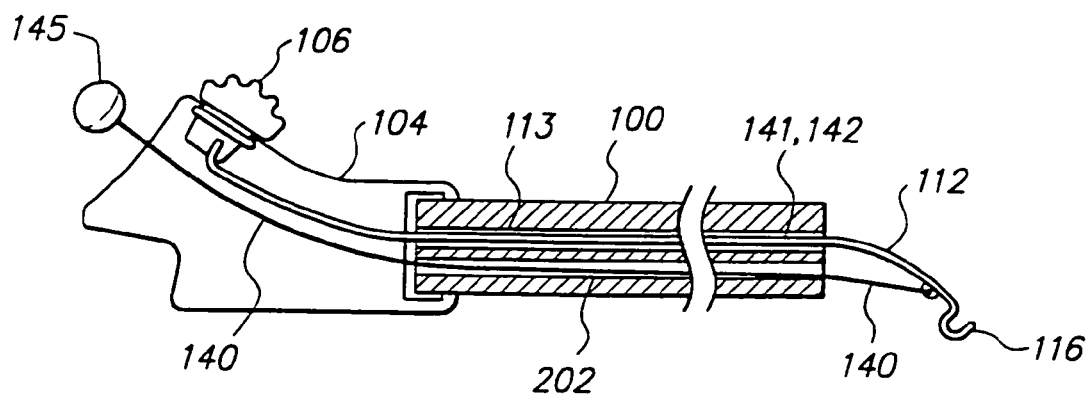
FIG. 6c is a cut-away side view of the angling device embodiment in which the angling device 140 is in a separate lumen from the retractor 112.

Upon extending the retractor 112 using button 106, the angling device 140 is extended with the retractor 112. The angling device 140 is coupled to a handle 145 at the proximal end of the cannula 100 to facilitate establishing an angle in the retractor 112 by pulling with a backward force on the angling device 140. As illustrated in FIG. 6b, after the retractor 112 is extended, the angling device 140 is actuated and a bend is created in the retractor 112 as the backward force exerted on the distal end of the retractor is exerted against the relatively fixed position of the retractor legs 141, 142 disposed within the lumens 113. As shown in FIG. 6c, the angling device 140 may also be located in a separate lumen 202 from the retractor 112 with part of the angling device 140 positioned outside of the cannula 100 when the retractor 112 is in the retracted position.

Figure 7A:
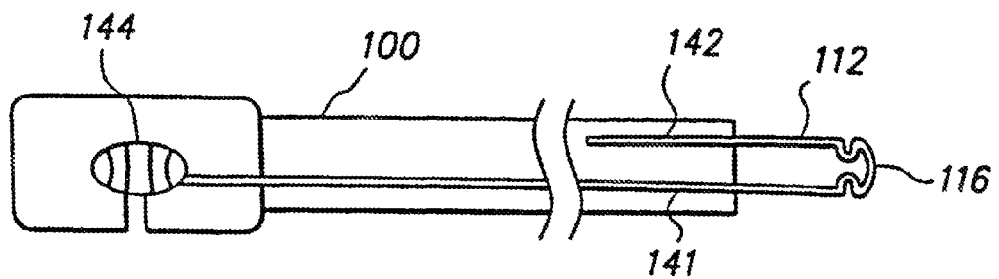
FIG. 7a is a cut-away side view of a twistable retractor 112 in a straight position.
Figure 7C:
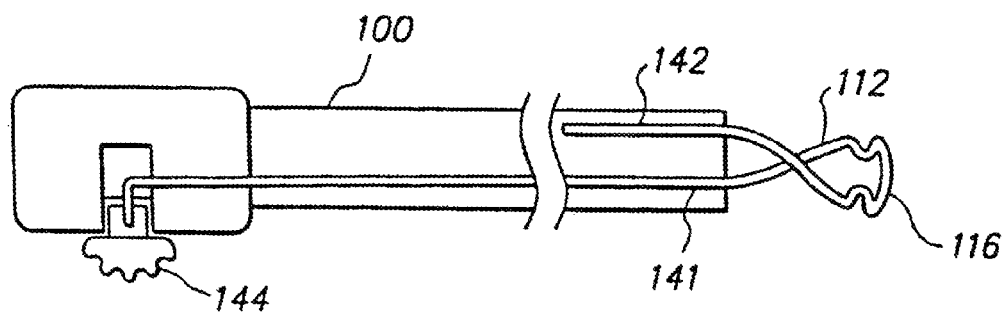
FIG. 7c is a cut-away side view of twistable retractor 112 in a crossed position.
Figure 7B:
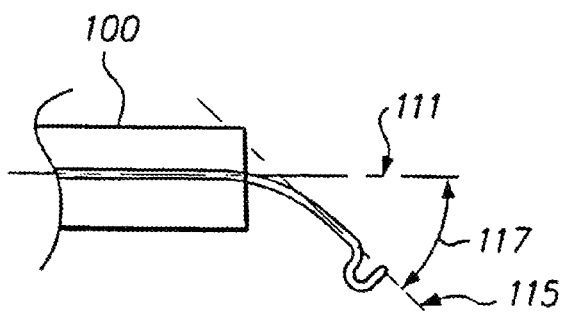
Figure 7D:
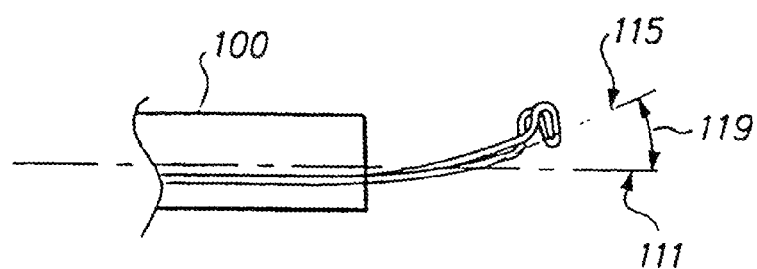
FIG. 7d is a side view of the retractor 112 of FIG. 7c.

FIG. 7a illustrates another embodiment of cannula 100 in which the retractor 112 is pre-formed with one leg 141 of the retractor 112 bent at an angle at its proximal end skewed to the axis of the distal end of the other leg 142. The bent portion of the leg 141 may be linked to a sliding knob 147 for convenient manual manipulation of this embodiment of the invention. Upon sliding the knob 147, the leg 142 coupled to knob 147 is twisted rotationally. The two legs 141, 142 of retractor 112 are coupled together via cradle 116. The axis of the second portion of the retractor 112 in the first position is at a first angle 117 to the axis of the cannula 100, as shown in FIG. 7b. As knob 147 is moved, leg 141 is rotated and crosses under leg 142, as shown in FIG. 7c. This causes cradle 116 to flip 180 degrees and bends the retractor 112 at a second angle 119, as shown in FIG. 7d. Thus, if a vessel is disposed on one side of cradle 116 or cannula 100 while the retractor 112 is in the first position, then upon rotating the knob 147, the vessel is transported to the other side of the cannula 100. This allows the user to isolate the vessel by simply actuating knob 147.

Figure 8A:
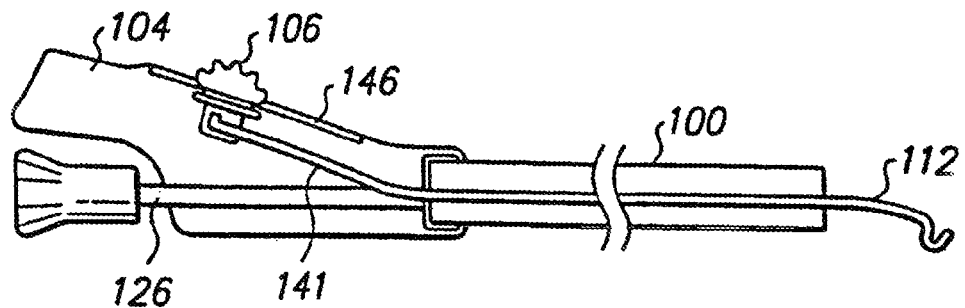
FIG. 8a is a cut-away side view of the handle 104.
Figure 8B:
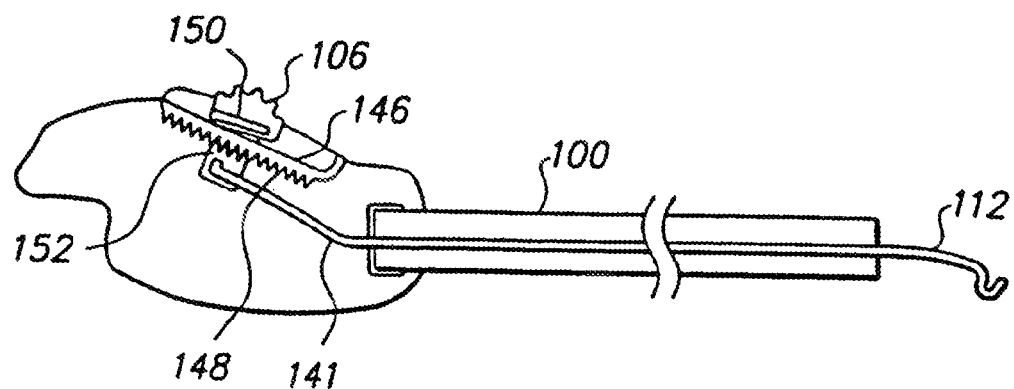
FIG. 8b is a cut-away side view of an alternate embodiment of handle 104.

FIG. 8a illustrates a cut-away side view of button 106 on the handle 104 of cannula 100, with an endoscope 126 positioned within cannula 100. As mentioned above, button 106 is coupled to one leg 141 of the proximal end of retractor 112. Sliding the button 106 in groove 146 translationally moves the retractor 112. Groove 146 is preferably minimally wider than the shaft of button 106 to minimize excessive horizontal movement of button 106 while still allowing smooth translational movement of button 106. As illustrated in FIG. 8b, the button 106 may include locking or ratcheting teeth 152 to give tactile feedback of its location, and to positively retain the button and the associated leg 141 in an extended or retracted position. Several mating teeth 148 are located underneath groove 146, and a spring member 150 is attached to button 106 to exert pressure against the base of groove 146, to engage mating teeth 148, 152. When a force is applied on the top of button 106, the interlocking sets of teeth are disengaged and button 106 can move freely. Upon achieving the desired extension or retraction of the leg 141, button 106 is released and is retained place by the engaged teeth 148, 152.

Figure 9A:
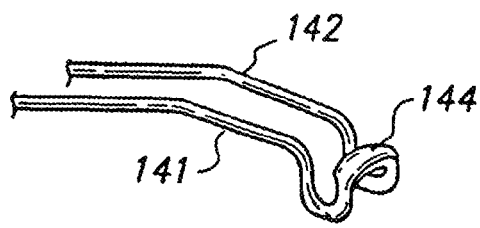
FIG. 9a is a side view of cradle 116.

FIG. 9a illustrates a top view of cradle 116 in an embodiment in which the cradle 116 is formed by two legs 141, 142 of retractor 112. The distal end of the legs form "U"-shaped side guides. The top 144 of the distal portion of the "U" is preferably flattened. This provides atraumatic support for the target vessel retained within cradle 116. Additionally, by minimizing the thickness of distal portion 144, contact with other devices in close proximity with retractor 112 is minimized.

Figure 9B:
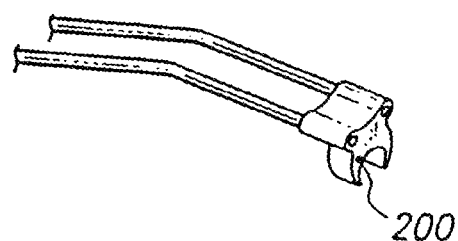
FIG. 9b illustrates a first alternate embodiment of cradle 116.

The cradle 116 may have other effective shapes, for example, as illustrated in FIG. 9b in which a "C" ring element is attached to legs of the cradle 116. The "C" ring may have a small hole 200 in one side with an axis approximately parallel to the axis of the retractor 112. This hole 200 is used to hold suture or other ligating materials, and may also be used as a knot pusher. As shown in FIGS. 10a and 10b, in an alternate embodiment of the embodiment of FIG. 9b, the retractor 112 is formed and flattened and a "C"-shaped ring is coupled to the retractor 112 by, for example, gluing or molding the "C" ring to the distal end of the retractor 112, as shown in FIGS. 10c and 10d.

Figure 9C:
FIG. 9c illustrates multiple views of a second alternate embodiment of cradle 116.
Figure 9D:
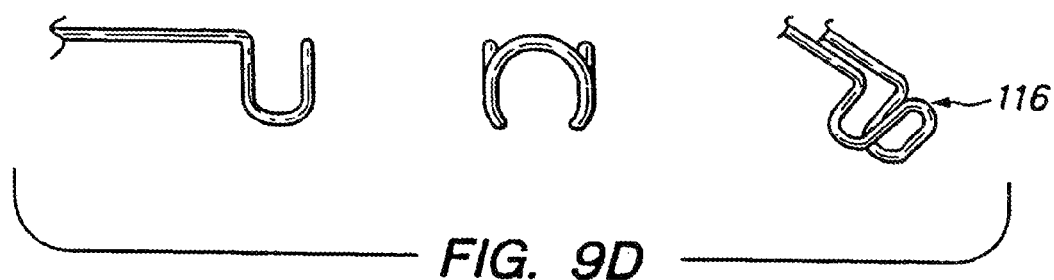
FIG. 9d illustrates multiple views of a third alternate embodiment of cradle 116.
Figure 9E:
FIG. 9e illustrates multiple views of a fourth alternate embodiment of cradle 116.

Referring back to FIGS. 9c, 9d, and 9e, the side guides of the cradle may include a loop 129 in a "V" shape, an arced "U" shape, or a semi-circular shape. In one embodiment, as illustrated in FIG. 9f, the retractor 112 has only one leg 141, and the cradle 116 is formed by the leg 141. A stopper 160 is coupled to the end of the leg 141 to serve as a guide to retain the target vessel, and add a blunt surface to the end of the wire, for example, for pushing and probing tissue. FIG. 9g illustrates a retractor 112 having a spur 204 formed in one or both legs 141, 142 for allowing the retractor 112 to be used for dissection. Sinusoidal, half-sinusoidal, and other geometric configurations may be used equally effectively as the shape of loop 129 in accordance with the present invention.

Figure 11A:
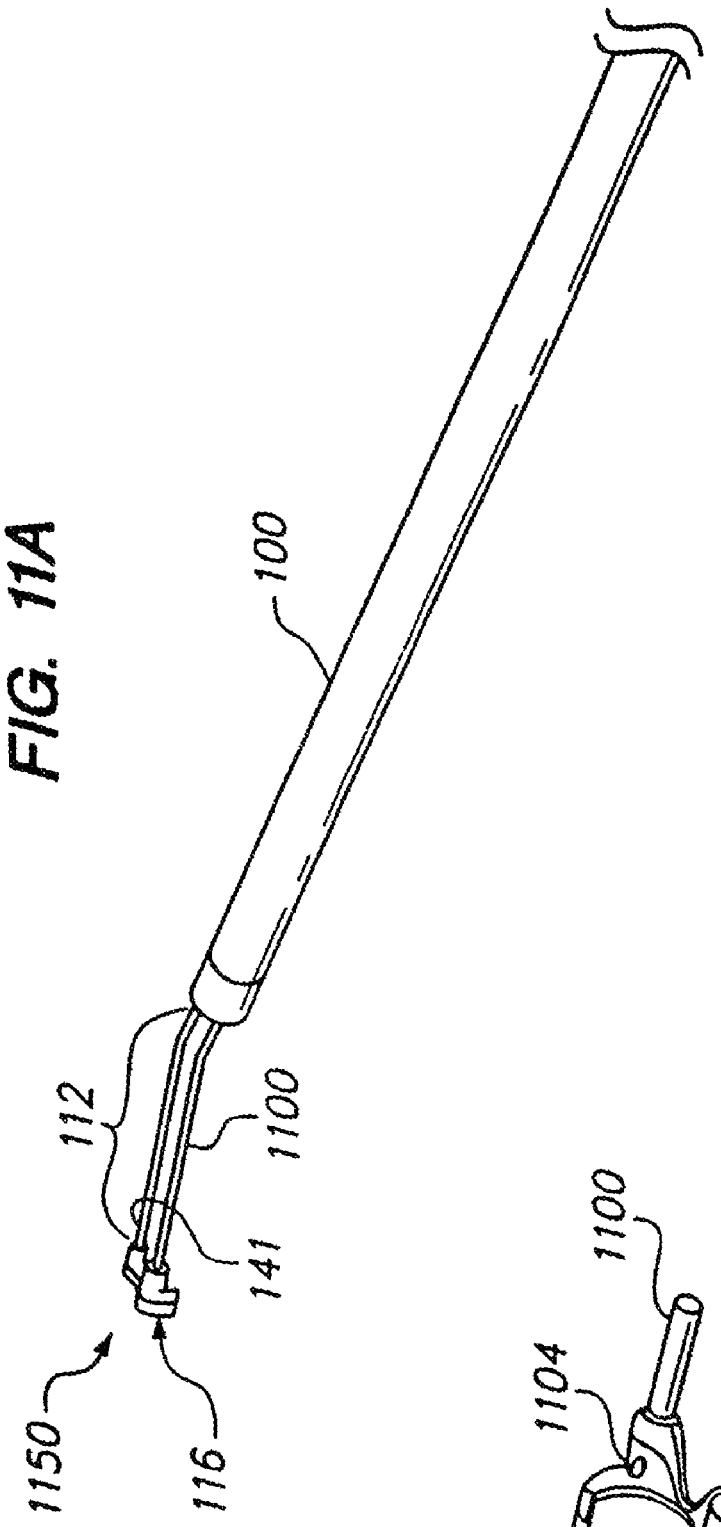
FIG. 11a illustrates a perspective side view of a cannula 100 including an irrigation system integrated with the retractor 112.
Figure 11B:
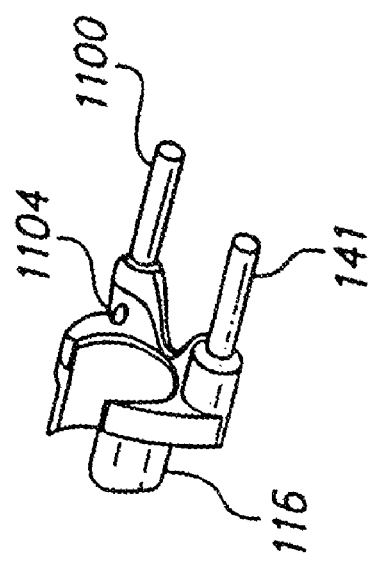
FIG. 11b is a cut-away view of a retractor 112 of FIG. 11a modified to incorporate the irrigation system.

FIG. 11a illustrates a perspective side view of a cannula 100 and an irrigation effector 1150 for cleaning an endoscope lens 1108 and wetting a surgical site. In the embodiment of FIG. 11a, the irrigation effector is retractor 112. As described above, the retractor 112 extends distal to the tip of the cannula 100 responsive to activation of a control button 106. In one embodiment, two supporting members 1100, 141 attach to the dissection cradle 116 and allow it to extend and retract. As shown in FIG. 11b, one supporter or leg 1100 is hollow, functioning as a lumen to carry irrigation fluid for cleaning an endoscope lens 1108 (shown in FIG. 11c). An irrigation nozzle 1104 is disposed on the cradle 116 or on the distal portion of the hollow leg 1100 and is configured to spray irrigation fluid at the endoscopic lens 1108. The irrigation fluid is received from a fluid source which conducts the fluid under pressure to the leg 1100. When the retractor 116 is slightly extended out of the distal end of the cannula 100, the irrigation nozzle 1104 is directed toward the lens 1108 of the endoscope 126 at an angle approximately normal to the endoscope lens 1108, allowing a spray of irrigation fluid to contact the surface of the lens 1108 and clean the lens 1108 effectively. Additionally, as the spray is directed back toward the endoscope 126, the surgeon is able to view the source of the spray through the endoscope 126, and is able to adjust the angle of incidence by adjusting the extension of the retractor 112. Thus, by having the endoscopic washing system built into the cannula 100 and into the sliding retractor 112, a more effective cleaning system is provided than what is provided by systems which are built into the endoscope itself.

If the surgical site requires irrigation, the dissection cradle 116 is extended out of the cannula 100, as shown in FIG. 11a, toward the area requiring irrigation. Upon reaching the site under endoscopic visualization, the surgeon can direct a spray of irrigation fluid toward the site. Again, if the site is not properly irrigated, the surgeon can adjust the positioning of the retractor 112 until the spray has contacted the surgical site. Thus, the irrigation system of the present invention can both wash the endoscope lens 1108 and irrigate a remote surgical site.

Figure 11C:
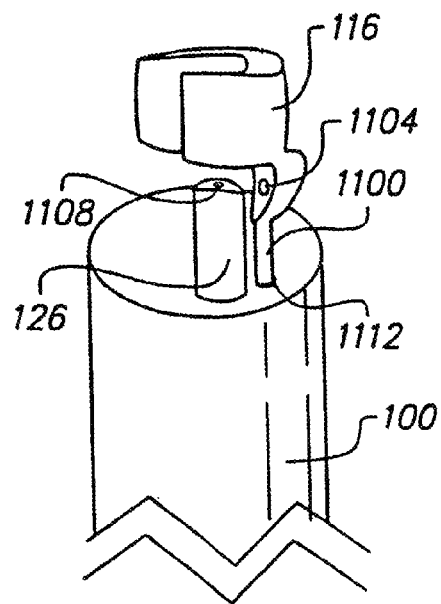
FIG. 11c is a cut-away view of a modified retractor 112 and endoscope 126 situated in a cannula 100.
Figure 11D:
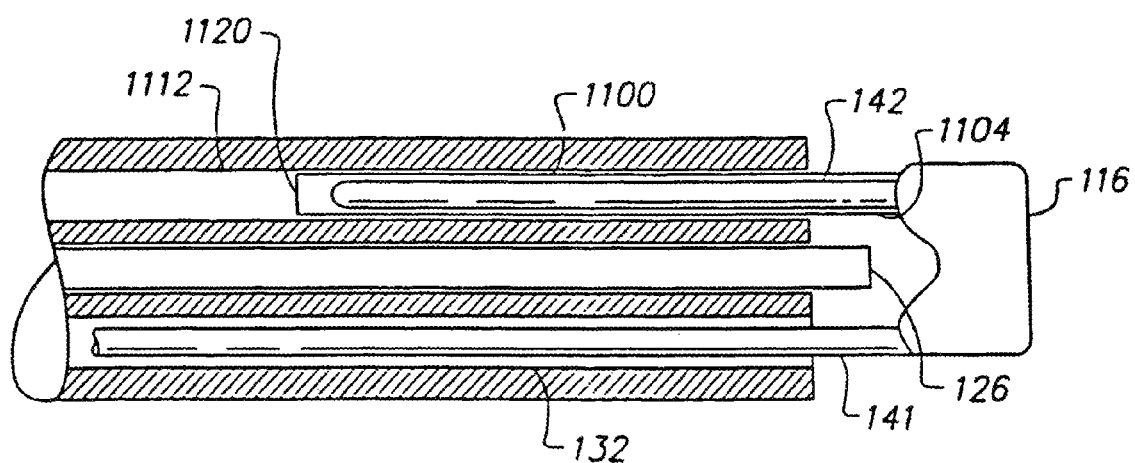

As shown in FIG. 11c, the hollow leg 1100 is situated within a lumen 1112 in the cannula body 100. An extension tube (not shown) is connected to the proximal end of the lumen 1112 to provide a source of irrigation fluid under pressure, for example, via a Luer lock syringe fitting. The syringe is used to selectively inject fluid under pressure into the lumen 1112 upon a determination that the endoscope lens 1108 requires cleansing. The hollow leg 1100 may extend only a fraction of the length of the lumen 1112 within the cannula body 100 prior to coupling to irrigation fluid under pressure. However, the hollow leg 1100 should be of sufficient length to extend the cradle 116 out to its proper working distance. To minimize leakage of irrigation fluid, the hollow leg 1100 has an outer diameter that slip fits within the inner diameter of the cannula body lumen 1112. Alternatively, as shown in FIG. 11d, the hollow leg 1104 has an outer diameter smaller than the inner diameter of the cannula body lumen 1112, but has a proximal end 1120 that flares out to a slip fit within the cannula body lumen 1112. These relative dimensions allow irrigation fluid to be dispensed through the cannula body lumen 1112, into the hollow leg 1100 and out the irrigation nozzle 1104 without significant leakage past the hollow leg 1100.

FIG. 11d illustrates an embodiment of the single-leg irrigation system in which a wire 141 is present within the hollow leg 1100 in lumen 113. The presence of wire 141 provides support and rigidity to the retractor 112 while retaining the ability of the hollow leg 1100 to be used to conduct irrigation fluid to the irrigation nozzle 1104.

Figure 12:
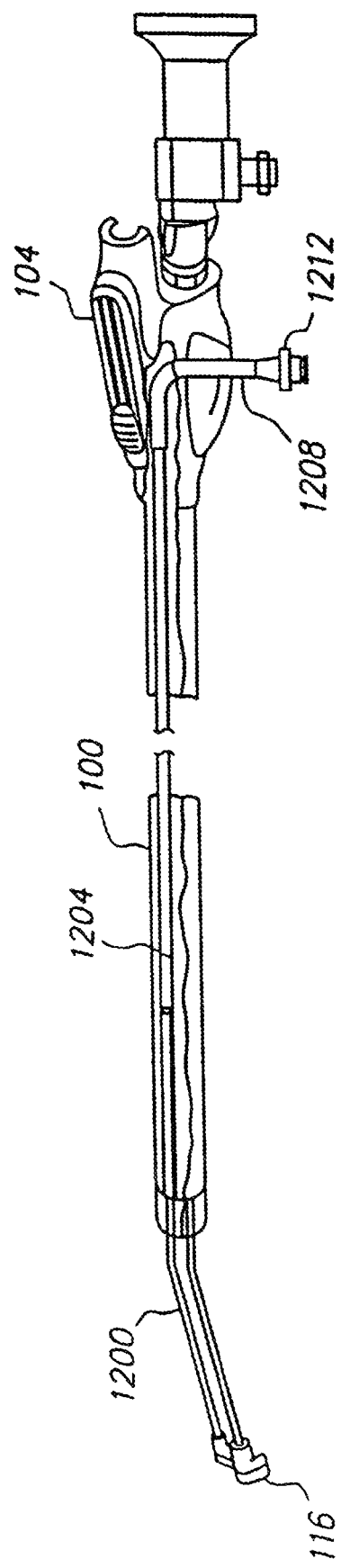
FIG. 12 is a cut-away side view of a multi-tube embodiment of an irrigation system.

FIG. 12 is a cut-away side view of a multi-tube embodiment of a cannula-based irrigation system. In this embodiment, the hollow leg 1200 includes a semi-rigid flexible tube or the like, and extends approximately one quarter to one third of the length of the cannula body 100 within a second irrigation tube 1204 inside of the cannula body lumen 1112. A fluid input tube 1208 of flexible plastic attaches to the proximal end of the irrigation tube 1204 and extends out of the cannula handle 104. The proximal end of the fluid input tube 1208 may include a valved Luer lock fitting 1212 for connection to a source of irrigation fluid such as provided by a syringe by selective applications of pressure. The first tube 1200 is slidable within the irrigation tube 1204 to form an adequate sliding fluid seal between the moving parts.

Figure 13:
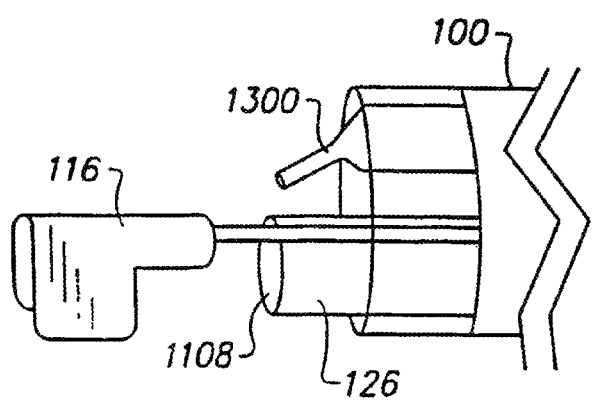
FIG. 13 is a cut-away side view of an irrigation system including a separate lumen.

FIG. 13 is a cut-away side view of a separate lumen irrigation system. In this embodiment, the cannula 100 contains a separate irrigation lumen in the cannula body. The lumen ends in a spray nozzle 1300 on the distal tip of the cannula 100. The tip of the nozzle 1300 is approximately parallel to the lens 1108. Cleansing is accomplished by applying spraying irrigation fluid across the lens 1108 to wash the lens 1108. The irrigation fluid is supplied to the irrigation lumen by a fluid input tube 1208 as described above in FIG. 12, and the proximal end of the fluid tube 1208 may be attached to a syringe as a source of the irrigation fluid under selective pressurization. The syringe may be removeably attached to the cannula handle 104 to prevent the syringe from moving or dangling from the handle 104, and obtruding on manipulation of the cannula 100 during vessel harvesting.

Figure 14A:
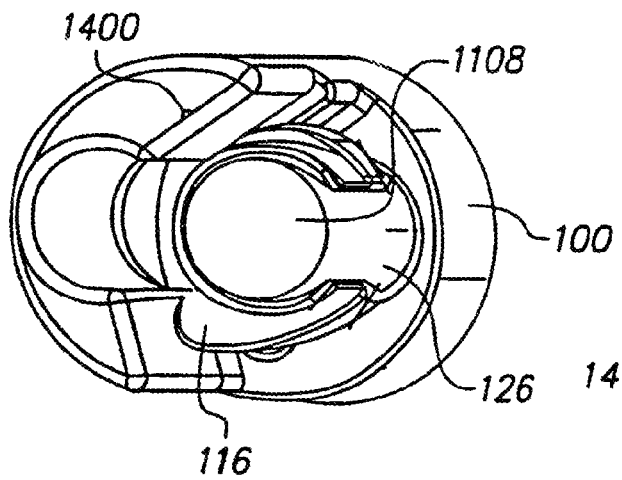
FIG. 14a is a perspective front view of a single leg irrigation system.
Figure 14B:
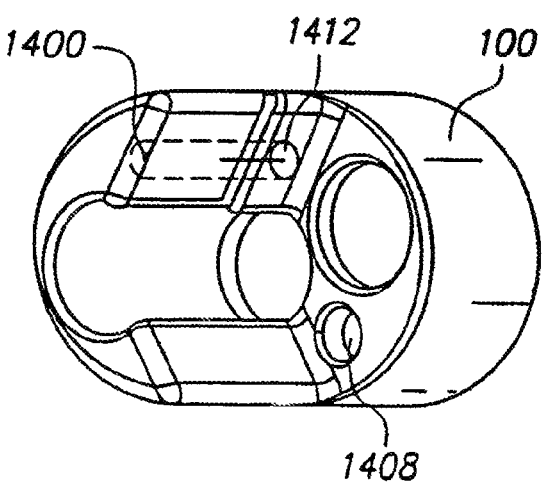
FIG. 14b is a perspective side view of the single leg irrigation system.

FIG. 14a is a perspective front view of a single leg irrigation system and shows the distal end of the cannula 100 housing the cradle 116 and the endoscope 126. In this embodiment, the dissection cradle 116 is supported by one leg 141 (shown in FIG. 11b) within a first lumen 1408 within the cannula body 100, and a cannula body lumen 1412 not occupied by the second leg of the cradle 116, as in embodiments previously described, is fitted with a nozzle 1400 which sprays the endoscope lens 1108. The spray nozzle 1400 is directed at an angle at which the endoscope lens 1108 can be sprayed directly and effectively for cleaning. FIG. 14b is a perspective side view of the single leg irrigation system and shows the distal end of the cannula 100 and the location of the spray nozzle 1400.

Figure 15:
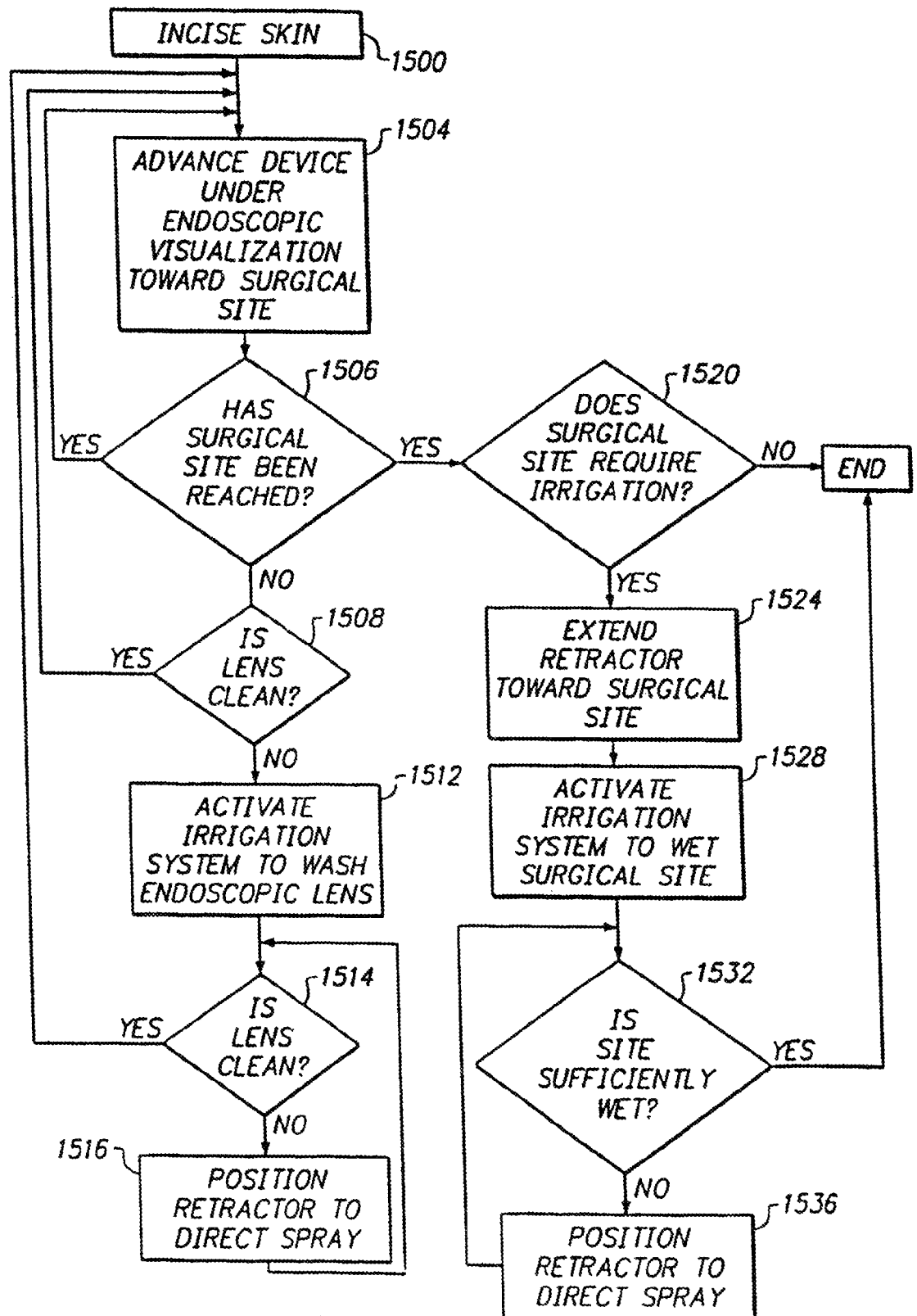
FIG. 15 is a flowchart illustrating a method of cleansing an endoscopic lens and irrigating a surgical site in accordance with the present invention.

FIG. 15 is a flowchart illustrating a method for washing an endoscopic lens 1108 and remote surgical site in accordance with the present invention. First, skin is incised 1500 at an area near a target vessel. Next, the device is advanced 1504 under endoscopic visualization toward the surgical site. If the surgeon determines 1506 that the surgical site has been reached, then the surgeon determines 1520 whether the surgical site requires irrigation. If the surgical site requires irrigation, the surgeon extends 1524 the retractor 112 toward the surgical site and activates 1528 the irrigation system to wet the surgical site. The surgeon determines 1532 whether the site is sufficiently wet by viewing the site through the endoscope 126. If the site is sufficiently wet, the process ends. If the site requires more irrigation, the surgeon positions 1536 the retractor 112 under endoscopic visualization to direct the spray more accurately at the surgical site.

If the surgical site has not been reached, the surgeon determines 1508 whether the lens 1108 is clean. In response to the lens 1108 becoming obscured with blood, fatty tissue, or the like, the irrigation system is activated 1512 in situ to wash the lens 1108. In one embodiment as described above, the retractor 112 is extended until the angle of the spray is approximately normal to the surface of the endoscopic lens 1108, and therefore effectively washes the lens 1108. Next, the surgeon determines 1514 whether the lens 1108 has been cleaned satisfactorily. If not, the retractor and thereby the irrigation nozzle 1104 is selectively positioned 1516 via extension or retraction of the retractor 112 under endoscopic visualization to direct the spray toward the lens 1108 at a more effective angle. The surgeon can continue to reposition the retractor 112 until the spray nozzle is directed at an effective angle toward the lens 1108.

Figure 16A:
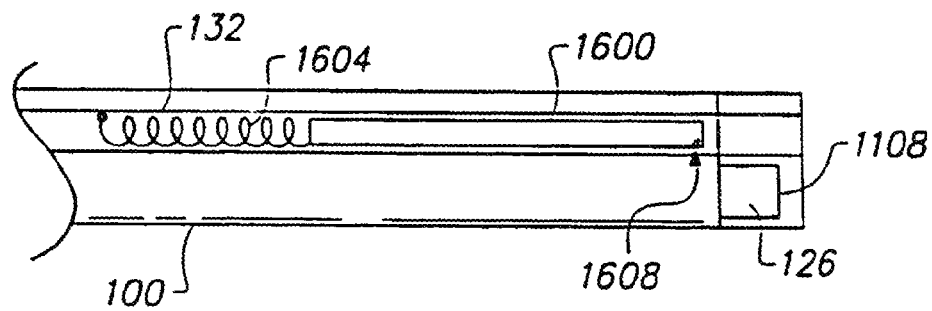
FIG. 16a is a cut-away side view of an alternate embodiment of a cannula-based irrigation system in accordance with the present invention.
Figure 16B:
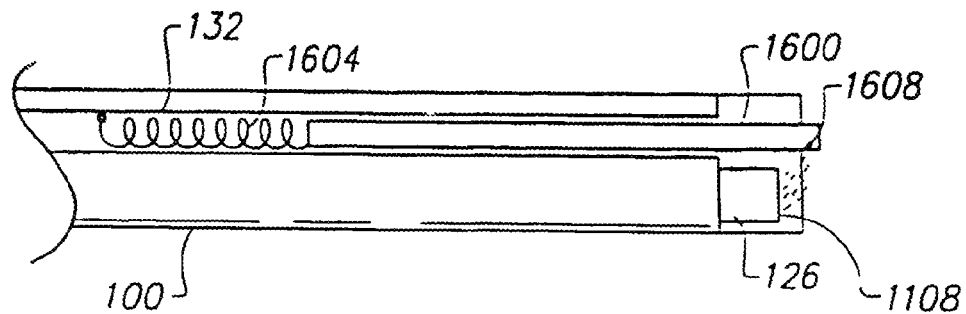
FIG. 16b illustrates the embodiment of FIG. 16a when the nozzle 1600 is under hydraulic pressure.

FIG. 16a shows a cut-away side view of another embodiment of a cannula-based irrigation system. In this embodiment, a nozzle tube 1600 is extendable from within a lumen 113 in the cannula 100. The proximal end of the nozzle tube 1600 is attached to a distal end of a tension spring 1604, whose proximal end is stably attached on the side of the lumen 113 or at the proximal end of the cannula 100. The tension spring 1604 biases the nozzle tube 1600 in a retracted state. Upon exposure to hydraulic water pressure, as shown in FIG. 16b, the liquid pushes the nozzle tube 1600 out of the lumen to a point slightly beyond the endoscope lens 1108. The liquid flows inside the nozzle tube 1600 and exits out the spray hole 1608, spraying irrigation fluid back towards the endoscope lens 1108.

Thus, the irrigation systems described above provide an effective method of cleaning an endoscope lens 1108 without requiring the removal of the endoscope from a surgical site. Additionally, the washing system described above is more effective due to the use of a spray nozzle external to the endoscope, which allows the angle of spray to be directly projected against the endoscope lens 1108. In an embodiment in which the irrigation nozzle 1104 is disposed on the cradle 116 or on the hollow leg 1100, a surgeon can visually adjust the angle of incidence of the spray, and can also irrigate a surgical site by adjusting the extension of the retractor 112 out of the cannula 100.

What is claimed is:

1. A surgical apparatus comprising:
   an elongated cannula having an elongated axis between distal and proximal ends of the cannula, and including an endoscope lumen extending as a hollow bore between the distal and proximal ends for slidably receiving an endoscope therein;
   an instrument lumen extending as a hollow bore between the distal and proximal ends of the cannula in substantial diametric orientation therein relative to the endoscope lumen;

a pair of auxiliary lumens disposed in substantially diametric orientation on opposite sides of, and in skewed relation to, the diametric orientation of the endoscope lumen and instrument lumen, at least one of the pair of auxiliary lumens extending between the distal and proximal ends of the cannula;

elongated supports slidably disposed within each of the pair of auxiliary lumens to selectively extend beyond the distal end of the cannula; and an end effector transversely mounted between distal ends of the respective elongated supports.

2. The surgical apparatus according to claim 1 in which the elongated supports are resiliently skewed laterally relative to the elongated axis of the cannula for lateral displacement therefrom in response to movement of the supports in a direction distally of the distal end.

3. The surgical apparatus according to claim 1 including a manual control element attached to at least one of the elongated supports, wherein the manual control element is located near the proximal end of the cannula and is disposed for manually activating sliding movement of the supports.

4. The surgical apparatus according to claim 1 in which the end effector includes a substantially U-shaped transverse segment between the elongated supports that is configured for positioning about an endoscope received in the endoscope lumen and protruding from the distal end of the cannula.

5. The surgical apparatus of claim 1, wherein the end effector is configured to displace a tissue laterally away from the elongated axis of the elongated cannula.

6. The surgical apparatus of claim 1, wherein the end effector has a portion for passively capturing a tissue.

7. The surgical apparatus of claim 1, further comprises an instrument at the distal end of the cannula for operating on tissue while the end effector applies tension to the tissue.

8. A surgical apparatus comprising:

an elongated cannula having a central axis oriented between distal and proximal ends of the cannula, and including a plurality of lumens extending between the distal and proximal ends of the cannula;

an elongated support having an end effector at its distal end and being slidably disposed within at least one of the plurality of lumens to selectively extend the end effector beyond the distal end of the cannula and away from the central axis thereof;

wherein the end effector includes a feature for deflecting tissue.

9. The surgical apparatus according to claim 8 in which the end effector has a recessed groove aligned substantially along the central axis.

10. The surgical apparatus according to claim 8 in which the elongated support is resiliently biased away from the central axis to deflect laterally away therefrom in response to slidable extension of the support beyond the distal end of the cannula.

11. The surgical apparatus according to claim 8 in which the elongated support comprises two legs, each leg disposed within each of a pair of the plurality of lumens, with the end effector mounted between distal ends of the respective legs of the elongated support.

12. The surgical apparatus according to claim 10 including an instrument lumen extending between distal and proximal ends of the cannula for receiving therein a surgical instrument that can be selectively extended beyond the distal end of the cannula with the end effector laterally deflected away from the central axis.

13. The surgical apparatus of claim 8, wherein the end effector is configured to displace the tissue laterally away from the central axis of the elongated cannula.

14. The surgical apparatus of claim 8, wherein the end effector has a portion for passively capturing the tissue.

15. The surgical apparatus of claim 8, wherein the feature comprises a structure that is fixedly mounted to the support.

16. The surgical apparatus of claim 15, wherein the support includes two support members, and the structure is fixedly mounted to the two support members and is located between the two support members.

17. The surgical apparatus of claim 8, further comprises an instrument at the distal end of the cannula for operating on tissue while the end effector applies tension to the tissue.

18. A surgical procedure performed on a patient with an elongated cannula having a central axis, a bore for receiving an endoscope therein and a support that is resiliently biased laterally away from the central axis and including an end effector mounted on a distal end of the support, the support being slidably mounted to selectively extend beyond a distal end of the cannula, the procedure comprising:

introducing the cannula into a body of the patient; and slidably extending the support and the end effector mounted thereon beyond the distal end of the cannula to effect lateral deflection of the end effector away from the central axis of the cannula, wherein the end effector includes a feature for deflecting tissue.

19. The surgical procedure according to claim 18 in which the tissue engaged with the end effector is laterally displaced away from the central axis in response to slidable extension of the support beyond the distal end of the cannula.

20. The surgical procedure according to claim 19, wherein the cannula includes an instrument lumen extending therethrough, the procedure further comprising:

introducing a surgical instrument through the instrument lumen for performing a procedure with the tissue laterally displaced from the orientation of the central axis of the cannula.

21. The surgical procedure according to claim 20 in which the cannula includes an actuator disposed near the proximal end thereof linked to the support, the procedure further comprising:

manually manipulating the actuator to selectively extend and laterally displace the distal end of the support within the patient's body away from the central axis of the cannula.

22. The surgical procedure of claim 18, wherein the end effector is used to displace the tissue laterally away from the central axis of the elongated cannula.

23. The surgical apparatus of claim 18, wherein the end effector has a portion for passively capturing the tissue.

24. The surgical procedure of claim 23, wherein the feature comprises a structure that is fixedly mounted to the support.

25. The surgical procedure of claim 24, wherein the support includes two support members, and the structure is fixedly mounted to the two support members and is located between the two support members.

26. The surgical procedure of claim 18, further comprises using an instrument at a distal end of the cannula to operate on target tissue while the end effector applies tension to the target tissue.

* * * * *